(12) United States Patent
Udrea et al.

(10) Patent No.: US 12,152,919 B2
(45) Date of Patent: Nov. 26, 2024

(54) THERMAL FLUID SENSOR

(71) Applicant: Flusso Limited, Cambridgeshire (GB)

(72) Inventors: Florin Udrea, Cambridgeshire (GB); Syed Zeeshan Ali, Cambridgeshire (GB); Ethan Gardner, Warwickshire (GB); Jonathan Owen Hardie, Cambridgeshire (GB); Jonathan Sean Callan, Cambridgeshire (GB)

(73) Assignee: Flusso Limited, Cambridgeshire (GB)

( * ) Notice: Subject to any disclaimer, the term of this patent is extended or adjusted under 35 U.S.C. 154(b) by 616 days.

(21) Appl. No.: 17/354,645

(22) Filed: Jun. 22, 2021

(65) Prior Publication Data

US 2022/0120701 A1   Apr. 21, 2022

Related U.S. Application Data

(63) Continuation-in-part of application No. PCT/EP2020/079575, filed on Oct. 21, 2020.

(51) Int. Cl.
   *G01N 25/18* (2006.01)
   *G01F 1/688* (2006.01)
   (Continued)

(52) U.S. Cl.
   CPC .............. *G01F 1/6888* (2013.01); *G01F 1/69* (2013.01); *G01F 1/7084* (2013.01); *G01N 25/18* (2013.01);
   (Continued)

(58) Field of Classification Search
   CPC ........ G01F 1/6888; G01F 1/69; G01F 1/7084; G01F 1/698; G01F 15/022; G01F 1/6845;
   (Continued)

(56) References Cited

U.S. PATENT DOCUMENTS 3,992,940 A   11/1976   Platzer, Jr.
4,548,078 A * 10/1985   Bohrer .................... G01F 1/698
                                            73/204.22
(Continued)

FOREIGN PATENT DOCUMENTS

DE   19919398 A1   5/2000
EP    2157411 A1   2/2010
(Continued)

OTHER PUBLICATIONS

EP20793693.1, "Office Action", issued Apr. 11, 2023, 7 pages.
(Continued)

*Primary Examiner* — Freddie Kirkland, III
(74) *Attorney, Agent, or Firm* — FisherBroyles, LLP

(57) ABSTRACT

We disclose herein a fluid sensor for sensing a concentration or composition of a fluid, the sensor comprising a semiconductor substrate comprising a first etched portion, a dielectric region located on the semiconductor substrate, wherein the dielectric region comprises a first dielectric membrane located over the first etched portion of the semiconductor substrate, a heating element located within the first dielectric membrane, and a first temperature sensing element spatially separated from the heating element. The fluid sensor further comprises a second temperature sensing element within the dielectric membrane, or the heating element may be further configured to operate as a second temperature sensing element. The separation between the second temperature sensing element and the first temperature sensing element introduces a temperature difference between the second temperature sensing element and the first temperature sensing element, such that a differential signal between the first temperature sensing element and the second temperature sensing element is indicative of the concentration or com-
(Continued)

position of the fluid based on a thermal conductivity of the fluid.

25 Claims, 27 Drawing Sheets

(51) Int. Cl.
    *G01F 1/69*     (2006.01)
    *G01F 1/7084*     (2022.01)
    *G01N 27/04*     (2006.01)
    *G01N 27/14*     (2006.01)
    *G01N 27/18*     (2006.01)
    *G01N 33/00*     (2006.01)
    *G01F 1/698*     (2006.01)
    *G01F 15/02*     (2006.01)

(52) U.S. Cl.
    CPC .............. *G01N 27/04* (2013.01); *G01N 27/14* (2013.01); *G01N 27/18* (2013.01); *G01N 33/0027* (2013.01); *G01F 1/698* (2013.01); *G01F 15/022* (2013.01)

(58) Field of Classification Search
    CPC ........ G01N 25/18; G01N 27/04; G01N 27/14; G01N 27/18; G01N 33/0027
    See application file for complete search history.

(56) References Cited

U.S. PATENT DOCUMENTS

| | | | |
|---|---|---|---|
| 4,944,035 | A | 7/1990 | Aagard |
| 5,321,983 | A | 6/1994 | Nagata |
| 5,804,720 | A | 9/1998 | Morimasa |
| 6,019,505 | A | 2/2000 | Bonne |
| 6,046,398 | A | 4/2000 | Foote |
| 6,375,279 | B1 | 4/2002 | Cassidy |
| 6,460,411 | B1 | 10/2002 | Kersjes |
| 8,667,839 | B2 | 3/2014 | Kimura |
| 8,689,608 | B2 | 4/2014 | Nakano |
| 10,288,575 | B2 | 5/2019 | Ali et al. |
| 10,345,130 | B2 | 7/2019 | Bentley et al. |
| 10,408,802 | B2 | 9/2019 | Kumar |
| 10,480,974 | B2 * | 11/2019 | Huang ....................... G01F 7/00 |
| 10,488,358 | B2 | 11/2019 | Udrea et al. |
| 10,598,621 | B2 | 3/2020 | Liu |
| 10,712,300 | B2 * | 7/2020 | Nakano ................... G01N 25/18 |
| 11,035,709 | B2 * | 6/2021 | De Luca ............... G01F 15/024 |
| 11,073,415 | B2 | 7/2021 | Udrea et al. |
| 11,639,864 | B2 * | 5/2023 | De Luca ............... G01F 1/6965 73/204.25 |
| 11,867,648 | B2 * | 1/2024 | Ali .......................... G01N 27/22 |
| 2001/0027684 | A1 | 10/2001 | Lotters et al. |
| 2002/0100316 | A1 | 8/2002 | James |
| 2003/0041664 | A1 | 3/2003 | Ariyoshi |
| 2005/0028580 | A1 | 2/2005 | Bauer et al. |
| 2007/0011867 | A1 | 1/2007 | Yao |
| 2007/0017285 | A1 | 1/2007 | Wang |
| 2007/0113644 | A1 | 5/2007 | Manaka |
| 2007/0204688 | A1 | 9/2007 | Dmytriw |
| 2009/0016403 | A1 | 1/2009 | Chen |
| 2009/0158859 | A1 | 6/2009 | Huang |
| 2009/0164163 | A1 | 6/2009 | Wang |
| 2010/0078753 | A1 | 4/2010 | Mehregany |
| 2010/0175468 | A1 | 7/2010 | Anzai |
| 2011/0030468 | A1 | 2/2011 | Chen |
| 2011/0154885 | A1 | 6/2011 | Nakano et al. |
| 2011/0211613 | A1 | 9/2011 | Hermann |
| 2012/0216629 | A1 | 8/2012 | Huang |
| 2014/0190251 | A1 | 7/2014 | Huang et al. |
| 2014/0190252 | A1 | 7/2014 | Huang et al. |
| 2016/0025660 | A1 | 1/2016 | Hepp |
| 2016/0195419 | A1 | 7/2016 | Hepp |
| 2016/0216144 | A1 | 7/2016 | Figi et al. |
| 2018/0143051 | A1 | 5/2018 | Bentley et al. |
| 2018/0306621 | A1 | 10/2018 | Hornung |
| 2019/0030909 | A1 | 1/2019 | Sato |
| 2019/0031906 | A1 | 1/2019 | Kim |
| 2019/0301906 | A1 | 10/2019 | Udrea et al. |
| 2019/0301909 | A1 | 10/2019 | Nakano et al. |
| 2020/0080951 | A1 | 3/2020 | Nakano et al. |
| 2021/0116281 | A1 | 4/2021 | Udrea et al. |
| 2021/0116282 | A1 * | 4/2021 | De Luca ............... G01F 1/6888 |
| 2022/0120702 | A1 * | 4/2022 | Udrea ................... G01F 1/6888 |
| 2022/0333966 | A1 * | 10/2022 | Udrea ................ G01N 33/0027 |

FOREIGN PATENT DOCUMENTS

| | | | |
|---|---|---|---|
| EP | 3367087 | A2 | 8/2018 |
| EP | 3392621 | A1 | 10/2018 |
| GB | 2558896 | A | 7/2018 |
| WO | 1998036247 | A1 | 8/1998 |
| WO | 2014102086 | A1 | 7/2014 |
| WO | 2021078776 | A1 | 4/2021 |

OTHER PUBLICATIONS

PCT/EP2022/067044, "International Search Report and Written Opinion", Jan. 4, 2023, 17 pages.
PCT/EP2022/067049, "International Search Report and Written Opinion", Dec. 29, 2022, 12 pages.
U.S. Appl. No. 16/658,711, Non-Final Office Action mailed on Nov. 5, 2020, 11 pages.
U.S. Appl. No. 16/658,711, Notice of Allowance mailed on Mar. 24, 2021, 13 pages.
Huijsing et al., Monolithic Integrated Direction-Sensitive Flow Sensor, Institute of Electrical and Electronics Engineers Transactions on Electron Devices, vol. 29, No. 1, Jan. 1982, pp. 133-136.
Kersjes et al., An Integrated Sensor for Invasive Blood-Velocity Measurement, Sensors and Actuators A: Physical, vols. 37-38, Jun.-Aug. 1993, pp. 674-678.
Kuklinski et al., Integrated-Circuit Bipolar Transistor Array for Fluid-Velocity Measurements, Medical & Biological Engineering & Computing, vol. 19, No. 5, Sep. 1981, pp. 662-664.
Kuo et al., Micromachined Thermal Flow Sensors—A Review, Micromachines, vol. 3, No. 3, Jul. 23, 2012, pp. 550-573.
Lofdahl et al., A Sensor Based on Silicon Technology for Turbulence Measurements, Journal of Physics E: Scientific Instruments, Jun. 1989, pp. 391-393.
Moser et al., Silicon Gas Flow Sensors Using Industrial CMOS and Bipolar IC Technology, Sensors and Actuators A: Physical, vol. 27, 1991, pp. 577-581.
Nguyen, Micromachined Flow Sensors—A Review, Flow Measurement and Instrumentation, vol. 8, No. 1, Mar. 1997, pp. 7-16.
International Application No. PCT/EP2020/079575, International Preliminary Report on Patentability mailed on May 5, 2022, 8 pages.
International Application No. PCT/EP2020/079575, International Search Report and Written Opinion mailed on Jan. 22, 2021, 10 pages.
Qin-Yi et al., A Novel CMOS Flow Sensor with Constant Chip Temperature (CCT) Operation, Sensors and Actuators, vol. 12, No. 1, Jul. 1987, pp. 9-21.
Sabate et al., Multi-Range Silicon Micromachined Flow Sensor, Sensors and Actuators A: Physical, vol. 110, No. 1-3, Feb. 1, 2004, pp. 282-288.
Van Der Wiel et al., A Liquid Velocity Sensor Based on the Hot-Wire Principle, Sensors and Actuators A: Physical, vol. 37-38, Jun.-Aug. 1993, pp. 693-697.
Van Oudheusden et al., Integrated Flow Friction Sensor, Sensors and Actuators, vol. 15, No. 2, Oct. 1988, pp. 135-144.
Van Oudheusden, Silicon Flow Sensors, IEE Proceedings, Part D—Control Theory and Applications, vol. 135, No. 5, Sep. 1988, pp. 373-380.
Van Oudheusden, Silicon Thermal Flow Sensors, Sensors and Actuators A: Physical, vol. 30, Nos. 1-2, Jan. 1992, pp. 5-26.

(56) References Cited

OTHER PUBLICATIONS

Van Putten, An Integrated Silicon Double Bridge Anemometer, Sensors and Actuators, vol. 4, May 31-Jun. 3, 1983, pp. 387-396.
Van Putten et al., Integrated Silicon Anemometer, Electronics Letters, vol. 10, No. 21, Oct. 17, 1974, pp. 425-448.
Wang et al., MEMS-Based Gas Flow Sensors, Microfluidics and Nanofluidics, vol. 6, No. 3, Jan. 8, 2009, pp. 333-346.
Yoon et al., An Integrated Mass Flow Sensor with On-Chip CMOS Interface Circuitry, Institute of Electrical and Electronics Engineers Transactions on Electron Devices, vol. 39, No. 6, Jun. 1992, pp. 1376-1386.
G. De Graaf et al., "Surface-micromachined thermal conductivity detectors for gas sensing." 2012 IEEE International Instrumentation and Measurement Technology Conference Proceedings, pp. 1861-1864.
Mahdavifar et al. "Simulation and Fabrication of an Ultra-Low Power miniature Microbridge Thermal Conductivity Gas Sensor," 2014 Journal of the Electrochemical Society, 161 B55.
Kommandur et. al., "A microbridge heater for low power gas sensing based on the 3-omega technique," Sensors and Actuators A 233 (2015) 231-238.

* cited by examiner

THERMAL FLUID SENSOR

TECHNICAL FIELD

The present disclosure relates to a micro-machined sensor, particularly but not exclusively, the disclosure relates to a fluid sensor for sensing concentration of a fluid or concentration of components of a fluid based on thermal conductivity of the fluid.

BACKGROUND

There is an increasing demand for gas sensors to monitor pollutants in our environment. Gas sensors can be based on many different principles and technologies. One such principle is using thermal conductivity to determine the composition of gases.

For example, in G. De Graaf and R. F. Wolffenbuttel, "Surface-micromachined thermal conductivity detectors for gas sensing." 2012 IEEE International Instrumentation and Measurement Technology Conference Proceedings, pp. 1861-1864, a thermal conductivity gas sensor based on silicon technology is described.

Mandavifar et. al. in "Simulation and Fabrication of an Ultra-Low Power miniature Microbridge Thermal Conductivity Gas Sensor," Journal of the Electrochemical Society, 161 B55, describe a device comprising a suspended thin polysilicon resistor that acts as a heater and a temperature sensor as part of a thermal conductivity sensor. The change in resistance of the polysilicon with temperature allows its use as a temperature sensor.

U.S. Pat. Nos. 10,598,621, 8,667,839B2, and 6,375,279B1, 8,689,608 and 10,408,802B2 describe further sensors. Kommandur et. al., "A microbridge heater for low power gas sensing based on the 3-omega technique," Sensors and Actuators A 233 (2015) 231-238, also describes a thermal conductivity sensor.

Many of the state-of-the-art devices use a differential signal between the main sensor and the reference. However, in all cases the reference device is a heater as well and thus doubles the power consumption of the device.

SUMMARY

Presently available sensors have, among others, the following disadvantages:
high power dissipation, low sensitivity and slow dynamic response of the sensor;
mechanical fragility and vibration sensitivity;
reduced mechanical robustness of sensor supporting structures;
complex fabrication processes;
manufacturing processes that are not fully CMOS compatible; and
manufacturing processes that are expensive.

The devices of the present disclosure are advantageous over the state-of-the-art devices for at least the following reasons:
the sensor is able to determine composition of a fluid and concentration of different components within the fluid, in a zero flow environment;
thermal isolation of the heated element which reduces power dissipation, increases sensitivity and provides a fast, dynamic response of the sensor;
reduced mechanical fragility and vibration sensitivity of the membrane structure compared to a beam structure;
a suitable dielectric material used for the dielectric membrane improves mechanical robustness of the membrane;
a suitable dielectric material (with low thermal conductivity) used for the dielectric membrane (with low thermal mass) reduces power dissipation, increases sensitivity and provides a fast, dynamic response of the sensor;
discontinuities within the membrane mitigate power dissipation, sensitivity and dynamic response issues; and
the devices are fully CMOS (Complementary Metal Oxide Semiconductor) and/or MEMS (Micro-Electro-Mechanical Systems) compatible and therefore can be manufactured using fully CMOS and/or MEMS compatible processes.

The presently disclosed fluid sensor is able to measure the composition of the fluid based on the different thermal conductivity of each of the components of the fluid.

Aspects and preferred features are set out in the accompanying claims.

According to a first aspect of the present disclosure, there is provided a first temperature sensing element spatially separated from the heating element, wherein the first temperature sensing element is located outside of the first dielectric membrane and over the semiconductor substrate, or wherein the first temperature sensing element is located on or within the first dielectric membrane and wherein the fluid sensor comprises at least one recessed region within the first dielectric membrane configured to thermally isolate the heating element from the first temperature sensing element, wherein the heating element is further configured to operate as a second temperature sensing element, and wherein the separation between the second temperature sensing element and the first temperature sensing element introduces a temperature difference between the heating element and the first temperature sensing element, such that a differential signal between the first temperature sensing element and the second temperature sensing element is indicative of the concentration or composition of the fluid based on a thermal conductivity of the fluid.

The first temperature sensing element is spatially separated from the heating element, so that the there is a temperature difference between the heating element and the first temperature sensing element. During operation of the heating element, the heat generated by the heater diffuses into the dielectric membrane, above and below the dielectric membrane, and into the fluid surrounding the heating element. The amount of heat lost to the fluid surrounding the heating element will depend on the thermal conductivity of the fluid. Therefore, a temperature profile of the heating element will depend on the thermal conductivity of the fluid within the sensor. Dependent on the thermal conductivity of the fluid, the heating element will use a different amount of power to heat to a given temperature.

The first temperature sensing element is outside the membrane, or within the dielectric membrane and thermally isolated from the heating element. Therefore, the temperature of the first temperature sensing element will remain at ambient or room temperature or at a significantly colder temperature than that of the heating element. As the temperature of the heating element is dependent on the heat conducted through the fluid within the sensor and thus the thermal conductivity of the fluid, the differential signal is also dependent on the thermal conductivity of the fluid. Different target fluids within the sensor have different thermal conductivities, and therefore the temperature of the second temperature sensing element (or the heating element)

can be used to determine the concentration or composition of the fluid within the sensor. The differential signal is indicative of a composition or concentration of the fluid, and the sensor may be further configured to determine the composition or concentration of the fluid based on the differential signal or the temperature of the first temperature sensing element. The change in power required or the temperature change due to heat loss to the fluid is generally small compared to the measured ambient temperature. Therefore, by measuring the differential signal the measured ambient temperature can effectively be cancelled out to improve measurement of the change in power required or the temperature change due to heat loss to the fluid. This can be done using a Wheatstone bridge, or schemes based on differential/instrumentation amplifiers.

The heating element is the same as the second temperature sensing element, i.e. the heating element operates as a resistive temperature detector. The heating element can be driven in a constant temperature, constant voltage or constant resistance mode, and instead of measuring the differential resistance between the first and second resistive temperature sensing elements, the differential voltage, current or power can be measured. When the thermal conductivity of the fluid around the sensor changes, the amount of voltage, current and/or power required to keep the heater at the same resistance or temperature will change, and thus the differential voltage/current/power between the first and second temperature sensing elements will change.

The heating element may be configured to operate as a sensing element by, for example, sensing the change in the resistance due to the change in temperature, as it is the case of resistive temperature detectors. The heating element may operate simultaneously as both a heating element and a sensing element. The heating element can be considered as electrically equivalent to a resistor. The electrical conductivity of most heaters materials (Tungsten, Titanium, Platinum, Aluminium, polysilicon, monocrystalline silicon) varies with temperature. This variation is mostly linear and is characterised by the TCR (Temperature coefficient of resistance). The TCR can be positive or negative, but most metals have a positive and stable TCR, meaning that their resistance increases when the temperature is increased.

The advantage of this embodiment is simplicity and reduced number of additional elements on the membrane. The larger the number of elements on the dielectric membrane, the higher the probability of impaired reliability or malfunction of the sensor.

By providing the first temperature sensing element on the substrate or on the same membrane and thermally isolated (i.e. not on a separate membrane), the first temperature sensing does not need to be separately heated. Therefore, the power consumption of the device is reduced.

In use, with no flow or static flow, this allows sensing of different components of a fluid using a differential signal between two sensing elements.

According to a further aspect of the disclosure, there is provided a fluid sensor for sensing a concentration or composition of a fluid, the sensor comprising: a semiconductor substrate comprising a first etched portion; a dielectric region located on the semiconductor substrate, wherein the dielectric region comprises a first dielectric membrane located over the first etched portion of the semiconductor substrate; a heating element located within the first dielectric membrane; a first temperature sensing element spatially separated from the heating element, wherein the first temperature sensing element is located outside of the first dielectric membrane and over the semiconductor substrate, or wherein the first temperature sensing element is located on or within the first dielectric membrane and wherein the fluid sensor comprises at least one recessed region within the first dielectric membrane configured to thermally isolate the heating element from the first temperature sensing element; and a second temperature sensing element located on or within the first dielectric membrane, wherein the second temperature sensing element is substantially identical in shape and size to the first temperature sensing element, and wherein the first temperature sensing element is located a first distance away from the heating element, and wherein the second temperature sensing element is located a second distance away from the heating element, and wherein the first distance is greater than the second distance, and wherein the separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

The fluid sensor may comprise a semiconductor substrate made of a semiconductor material such as silicon, silicon carbide or Gallium Nitride, and comprising an etched portion. The fluid sensor may also comprise a dielectric region comprising of oxides and/or nitrides such as silicon dioxide and silicon nitride, where the portion of the dielectric region adjacent to the etched portion is referred to as a dielectric membrane. The dielectric membrane may have embedded structures made of semiconductor material or metal structures.

The semiconductor substrate may be any semiconductor such as silicon, silicon on insulator (SOI), Silicon Carbide, Gallium Nitride or Diamond. In particular, the use of silicon is advantageous, as it guarantees sensor manufacturability in high volume, low cost and high reproducibility. The use of a silicon substrate could also enable on-chip circuitry for sensor performance enhancement and system integration facilitation. Such on-chip circuitry could be implemented by using analogue or digital or mixed-signal blocks placed outside the dielectric membrane.

The dielectric membrane or multiple dielectric membranes may be formed by back-etching using Deep Reactive Ion Etching (DRIE) of the substrate, which results in vertical sidewalls and thus enabling a reduction in sensor size and costs. However, the back-etching can also be done by using anisotropic etching such as KOH (Potassium Hydroxide) or TMAH (TetraMethyl Ammonium Hydroxide) which results in sloping sidewalls. The dielectric layers within the membrane which could be formed by oxidation or oxide deposition could be used as an etch stop during the DRIE or wet etching processes. The membrane can also be formed by a front-side etch (using most commonly wet etch techniques) or a combination of a front-side and back-side etch to result in a suspended membrane structure, supported only by two or more beams. The membrane may be circular, rectangular, or rectangular shaped with rounded corners to reduce the stresses in the corners, but other shapes are possible as well.

Preferably, the semiconductor substrate may be silicon and the dielectric membrane may be formed mainly of oxide and nitride materials, or oxinitride (a pre-formed combination of oxide and nitride) and where the heater element may be made of a metal such as tungsten, titanium, copper, aluminium, gold, platinum or a combination of those or a semiconductor such as highly doped n type or p type silicon or polysilicon. The heater may have a shape of a meander, spiral or a hotwire.

The dielectric region may comprise a dielectric layer or a plurality of layers including at least one dielectric layer. The dielectric region may comprise layers of more than one material, such as silicon dioxide, silicon nitride, or aluminium oxide. The heating element may be fully embedded or partially embedded within the dielectric membrane.

The membrane may also comprise one or more layers of spin on glass, and a passivation layer over the one or more dielectric layers. The employment of materials with low thermal conductivity (e.g. dielectrics) enables a significant reduction in power dissipation as well as an increase in the temperature gradients within the membrane with direct benefits in terms of sensor performance (e.g. sensitivity, frequency response, range, etc.). Temperature sensing elements or heaters made of materials such as monocrystalline or polycrystalline semiconductors or metals could be suspended or embedded in the dielectric membrane.

The dielectric membrane may also have other structures made of metal or other conductive or other materials with higher mechanical strength. These structures can be embedded within the membrane, or may be above or below the membrane, to engineer the thermo-mechanical properties (e.g. stiffness, temperature profile distribution, etc.) of the membrane and/or the fluid dynamic interaction between the fluid and the membrane. More generally, these structures can be also outside the membrane and/or bridging between inside and outside the membrane.

Generally speaking, a dielectric membrane region may be located immediately adjacent or above (or below if a flip-chip technology is used) to the etched portion of the substrate. The dielectric membrane region corresponds to the area of the dielectric region directly above or below the etched cavity portion of the substrate. Each dielectric membrane region may be over a single etched portion of the semiconductor substrate. The membrane may be a "closed membrane", supported by the substrate along its entire perimeter, or can be a bridge type structure—supported by a number of dielectric beams.

The fluid sensor may be configured to sense or measure a fluid (this may be a gas but could also be a liquid), and the gas may be made of air and the components of interest could be any of $CO_2$, methane or hydrogen or other gases in dry air or humid air. The component of interest can be any fluid that has a different thermal conductivity than that of air.

The disclosed sensor could be applicable to a variety of gases and liquids, but we make specific reference to Carbon dioxide ($CO_2$), methane and hydrogen as these specific gases have thermal conductivity properties which are significantly different from those of air.

The sensor may be a thermal conductivity fluid sensor incorporated in a MEMS structure comprising a heating element and at least one other sensing element (such as a temperature sensing element) that may be able to detect separately the fluid flow properties, such as velocity, volume flow rate, mass flow rate. The temperature sensing element may be able to also detect the composition the fluid based on the difference in thermal conductivity, specific heat capacity, dynamic viscosity, density (and other thermo-mechanical properties, hereafter simply referred to as thermal properties) of different components of the fluid.

During operation of the heating element, the heat generated by the heater diffuses into the dielectric membrane, above and below the dielectric membrane, and into the fluid surrounding the heating element. The amount of heat lost to the fluid surrounding the heating element will depend on the thermal conductivity of the fluid. Therefore, a temperature profile of the second temperature sensing element will depend on the thermal conductivity of the fluid within the sensor. Dependent on the thermal conductivity of the fluid, the heating element will use a different amount of power to heat the second temperature sensing element to a given temperature. As the temperature of the second temperature sensing element is dependent on the heat conducted through the fluid within the sensor between the heating element and the second temperature sensing, the temperature of the second temperature sensing element is dependent on the thermal conductivity of the fluid. Therefore, the differential signal is also dependent on the thermal conductivity of the fluid. Different target fluids within the sensor have different thermal conductivities, and therefore the differential signal can be used to determine the concentration or composition of the fluid within the sensor. The differential signal is indicative of a composition or concentration of the fluid, and the sensor may be further configured to determine the composition or concentration of the fluid based on the differential signal.

There may be a circuit to measure a differential signal between the first and second resistive temperature detector elements and use it to determine the concentration of a fluid or particular fluid components based on different thermal conductivities.

The first temperature sensing element may be located a first distance away from the heating element, and the second temperature sensing element may be located a second distance away from the heating element, and wherein the first distance may be greater than the second distance.

The second temperature sensing element may be located closer to the heating element than the first temperature sensing element. Preferably, the second temperature sensing may be located such that the second temperature sensing element has the same temperature as the heating element during operation of the sensor.

The differential signal may be measured as a temperature difference, voltage difference, current difference, power difference, or resistor difference.

The difference in the resistance of, current through, or voltage across the two resistive temperature detectors can be measured and this gives an indication of the composition of the fluid and the concentration of its one or more components. If the composition of the fluid (or concentration of a component of the fluid) around the sensor changes, its thermal conductivity also changes and this will change the thermal losses and the temperature of the heater—in turn changing the resistance of the second resistive temperature detector, without changing (or changing insignificantly) the resistance of the first temperature resistive temperature detector. The change in resistance could be measured directly, or could be measured as a voltage change, current change or power change.

Thus the difference in resistances (or voltages or currents) between the first and second temperature sensing elements allows measurement of the thermal conductivity of the surrounding fluid, and hence the composition of the surrounding fluid. Changes in ambient temperature affect both temperature sensing elements almost equally and hence does not affect significantly the difference in resistances.

The first temperature sensing element and the second temperature sensing element may be both located on or within the first dielectric membrane, and the fluid sensor may comprise at least one recessed region within the first dielectric membrane configured to thermally isolate the heating element and the second temperature sensing element from the first temperature sensing element.

The second temperature sensing element may be located in a same layer of the dielectric region as the heating element and the second temperature sensing element may laterally surround the heating element.

Alternatively, the second temperature sensing element may be located below or above the heating element. The second temperature sensing element may be located directly above or below the heating element, so that the second temperature sensing element is not laterally spaced from the heating element.

Having the second temperature sensing element in a same layer or below or above the heating element has the advantage that the temperature of the second temperature sensing element is substantially the same of that of the heater. This increases the differential signal between the first temperature sensing element and the second temperature sensing element, therefore improving sensitivity of the sensor.

The second temperature sensor element can be either laterally spaced but close to the heating element, and can be made of the same material layer as the heating element. Alternatively, the second temperature sensing element can be made of a different material layer than the heater and can be vertically spaced from the heater, either above or below the heater. An advantage of both these configurations is that the second temperature sensing element should have substantially the same temperature as the heater element during operation.

The two temperature resistive detectors can be identical in size, shape and resistance. Alternatively, the first temperature sensing element may be configured to have a higher resistance at room temperature than a resistance of the second temperature sensing element at room temperature, and the first temperature sensing element and the second temperature sensing element may be configured to have substantially the same resistance at an operating temperature of the sensor without a fluid present.

The semiconductor substrate may comprise an additional etched portion, and the dielectric layer may comprise an additional dielectric membrane located over the additional etched portion of the semiconductor substrate. The sensor further may comprise an additional heating element located within the additional dielectric membrane and an additional first temperature sensing element and an additional second temperature sensing element.

The heating element may be a resistive heating element. At least one of the first temperature sensing element and the second temperature sensing may be resistive temperature sensing elements, also known as resistive temperature detectors (RTDs).

The resistive temperature detector elements may comprise metal (Tungsten, Al, Copper, Platinum, Gold, Titanium) or semiconductor material (Silicon, Polysilicon, Silicon Carbide, Gallium Nitride, Aluminium Gallium Nitride, or Gallium Arsenide or a two dimensional electron gas)

Firstly, for increased sensitivity and stability, such resistive temperature detectors may have a high, reproducible and stable TCR (Temperature Coefficient of Resistance). Secondly, it is preferable that such resistive temperature detectors are linear in temperature (i.e. their resistance varies linearly with the temperature).

The sensing elements may be temperature sensitive and may be any of resistive temperature detectors, diodes, transistors or thermopiles, or an array in series or parallel or a combination of those.

Such sensors can be implemented in bulk COMOS, SOI (Silicon on Insulator) CMOS technology. SOI membranes can be made by using the buried oxide as an etch stop. SOI diodes, transistors and thermopiles can be made by using the thin silicon layer above the buried oxide which can be doped n or p-type.

One type of sensing element may be used or a combination of different types of sensing elements may be used.

A thermopile comprises one or more thermocouples connected in series. Each thermocouple may comprise two dissimilar materials which form a junction at a first region of the membrane, while the other ends of the materials form a junction at a second region of the membrane or in the heat sink region (substrate outside the membrane area), where they are connected electrically to the adjacent thermocouple or to pads for external readout. The thermocouple materials may comprise a metal such as aluminium, tungsten, titanium or combination of those or any other metal available in the process. Alternatively, the thermocouple materials may comprise thermocouples based on n-type and p-type silicon or polysilicon or combinations of metals and semiconductors. The position of each junction of a thermocouple and the number and the shape of the thermocouples may be any required to adequately map the temperature profile distribution over the membrane to achieve a specific performance.

The sensitivity and selectivity to the flow composition may be enhanced by using extra sensing elements, symmetrical or asymmetrical recessed regions, and/or an additional heater.

The first temperature sensing element may be located above the semiconductor substrate. The first temperature sensing element may be directly above the semiconductor substrate, so that the first temperature sensing element is completely above a substrate portion of the substrate and is not above the etched region of the substrate and is not located within the dielectric membrane. This increases thermal isolation between the first temperature sensing element and the components within the dielectric membrane, therefore improve the sensitivity of the device.

The first temperature sensing element may be located within the dielectric region, but preferably outside the dielectric membrane area or at an edge of the membrane area.

Alternatively, the first temperature sensor could also be placed at the edge of the membrane region (in order for example to reduce the chip area).

The fluid sensor may further comprise circuitry configured to determine the concentration or composition of the fluid based on the temperature of the first temperature sensing element or the differential signal.

There may be control circuitry that measures the differential signal between the first and second temperature sensor elements and uses it to determine the concentration of a fluid or particular fluid components based on different thermal conductivities.

A control and measurement unit/circuitry that drives the heater in constant current, constant voltage or constant power mode may be provided. The driving could be preferably in pulse mode, but continuous mode or AC mode are also possible.

The circuitry may be located on a same chip as the fluid sensor. Analogue/digital circuitry may be integrated on-chip. Circuitry may comprise IPTAT, VPTAT, amplifiers, analogue to digital converters, memories, RF communication circuits, timing blocks, filters or any other mean to drive the heating element, read out from the temperature sensing elements or electronically manipulate the sensor signals. For example, it is demonstrated that a heating element driven in constant temperature mode results in enhanced performance and having on-chip means to implement this driving method would result in a significant advancement of the state-of-the-art flow sensors. The driving method known a 3ω may be implemented via on-chip means, or any other driving method, such as constant temperature difference and time of flight, needed to achieve specific performance (e.g. power dissipation, sensitivity, dynamic response, range, fluid property detection, etc.). In absence of on-chip circuitry, this disclosure also covers the off-chip implementation of such circuital blocks when applied to a fluid sensor. Such off-chip implementation may be done in an ASIC or by discrete components, or a mix of the two.

The circuitry may comprise one or more of:
a constant current or constant resistor drive circuit,
a constant current source,
a Wheatstone bridge,
an amplifier, an Analog to Digital convertor,
a Digital to Analog Convertor, or
a microcontroller.

Differential signals can be obtained by using a combination of current sources and differential amplifiers, bridge type circuits or other types of subtraction circuits or instrumentation amplifiers.

The first temperature sensing element and the second temperature sensing may be located on two sides of a bridge circuit (also referred to as an instrumentation bridge, and can be a Wheatstone bridge), and the sensor may be configured such that an output of the bridge circuit may be a function of the thermal conductivity of the fluid around the sensor. The output of the bridge circuit may therefore also be a function of the concentration of particular fluid components with different thermal conductivities.

The first resistive temperature detector and second temperature detector may be placed together with other components on the sides of an instrumentation bridge, such as a Wheatstone bridge, and the differential output of the bridge could be a function of the thermal conductivity of the fluid around the sensor and the concentration of particular fluid components with different thermal conductivities. Such differential signals can be further amplified by using amplifiers, either located on the same chip, to maintain low noise, or placed within the same package, module or system.

The fluid sensor may comprise at least one recessed region within the first dielectric membrane and between the heating element and the first temperature sensing element.

The recessed region may be located between the first temperature sensing element and the second temperature sensing element—therefore there is a greater recessed volume between the heating element and the first temperature sensing element than between the heating element and the second temperature sensing element, such that the recessed region introduces a temperature difference between the first temperature sensing element and the second temperature sensing element due to differences in heat conduction through the dielectric membrane.

There may be no recessed region between the heating element and the second temperature sensing element so that the second temperature element is at substantially the same temperature as the heating element during operation of the device.

The recessed regions or discontinuities in the dielectric membrane provide an interruption (or partial interruption) in the thermal conduction path through the solid of the dielectric membrane. This in turn will mean that the heat path will occur more through the fluid above the recess (via conduction and convention) or through the cavity space formed as a result of the recess (mainly through fluid conduction). In both cases (heat above the cavity space or within the cavity space), the heat dissipation will depend on the thermal conductivity of the fluid. This increases the sensitivity of the differential signal to the thermal conductivity of the fluid.

The at least one recessed region may comprise one or more discontinuous regions where the thickness of the dielectric membrane is discontinuous or varies from an average or most common dielectric membrane thickness.

The at least one recessed region may be located between the heating element and an edge of the dielectric membrane.

An edge of the dielectric membrane may refer to a perimeter edge of the dielectric membrane, in other words, the area where the dielectric membrane meets or joins the semiconductor substrate. The area of the dielectric region above the semiconductor substrate may refer to the area of the dielectric region outside the dielectric membrane.

The recessed region may be located between the heating element and the edge of the dielectric membrane spaced from the heating element. In particular, the recessed regions may be defined such that there is one recessed region between the heating element and the edge of the membrane, one recessed region between the first temperature detector element and the edge of the membrane, and no recessed region between the heater and the first temperature detector element.

The recessed regions may be holes (perforations) through the dielectric membrane. This would be advantageous, as the thermal conduction path through the solid of the dielectric membrane will be impeded and this will mean that the thermal conduction will occur through the holes (mainly via conduction) or above the holes (via both conduction and convection), thus facilitating the measurement of the composition of the fluid based on the different thermal conductivity of each of the components of the fluid.

There may be at least one hole through the membrane to connect the upper side of the membrane to the lower side of the membrane via the fluid to be sensed. The at least one hole also disrupts the thermal conduction path through the solid dielectric membrane, forcing more heat to dissipate via convection and conduction through the environment. The presence of the at least one hole also helps to reduce the power consumption of the device (for the same heater temperature), because of the reduction in the heat conduction losses (through the solid membrane). Furthermore, the presence of the at least one hole allows for a lower thermal mass of the membrane thus reducing the time needed for the heater to heat up and cool down.

The at least one hole or recessed region may be used to enhance the sensitivity/selectivity to any fluid or component of the fluid (e.g. air with a concentration of $CO_2$) with a thermal conductivity that is different to that of a reference fluid or another component of the fluid (e.g. air).

An arrangement and specific design of different holes and different sensing elements is provided to enhance the sensitivity to any fluid or component of the fluid (e.g. air with a concentration of $CO_2$) with a thermal conductivity that is different to that of a reference fluid or another component of the fluid (e.g. air).

The arrangement of different holes or slots (or recessed regions) may be placed symmetrically around the heating element and the second temperature sensing element.

The at least one recessed region may comprises one or more holes. The holes may refer to apertures, perforations or slots extending through an entire height or depth or thickness of the dielectric membrane. This forms a fluid flow path and provides fluid connection between area above and area below membrane.

The at least one of the one or more holes may comprise an elongate slot extending towards opposite edges of the dielectric membrane. The elongate slot may not extend completely to the edges of the dielectric membrane or completely isolate the dielectric membrane either side of the elongate slot. The elongate slot increases thermal isolation across a width of the dielectric membrane of the device. Optionally the elongate slot may be extending in a same direction as one or more heating elements and/or sensing elements. The elongate slots may be, for example, rectangular, square, or semicircle.

The one or more holes may comprise an array of perforations. The perforations may comprise individual holes significantly smaller than a width of the dielectric membrane of the device. The array of perforations may can extend substantially across a width of the device.

The at least one recessed region may comprise a partial recess within the dielectric membrane. The partial recess or trench may extend from a top surface of the dielectric membrane or may extend from a bottom surface of the dielectric membrane. The partial recess may extend partially through a height or depth or thickness of the dielectric membrane. The at least one perforation may be in the form of a trench formed from the top or the bottom surface but not penetrating the other surface.

The discontinuities may be referred to as a gap in the membrane from the top surface to the bottom surface. Though, not as effective in terms of the thermal performance, a discontinuity could also refer to a trench or partial hole created from either the top or the bottom surface (if an upside-down membrane is used) without penetrating the other surface. The advantage of such partial holes is that they could impact less the mechanical strength of the membrane and in some cases they may be easier to be manufactured. Moreover, such partial holes could be used to hermetically seal the bottom side of the membrane or allow no fluid penetration below the membrane.

The at least one recessed region may have a meander shape. In other words, the discontinuity may have a non-standard shape such as a concertina or corrugated shape formed of a series of regular sinuous curves, bends, or meanders.

The etched region of the semiconductor substrate may have sloped sidewalls. The etched region of the semiconductor substrate may not extend through the entire depth of the semiconductor substrate.

The semiconductor substrate may comprise an additional etched portion, and the dielectric layer may comprise an additional dielectric membrane located over the additional etched portion of the semiconductor substrate. The sensor may further comprise an additional heating element located within the additional dielectric membrane, and an additional first temperature sensing element.

The additional heating element and the additional first temperature sensing element may operate similar to the heating element and first temperature sensing element. This increases sensitivity of the device.

The heating element and the additional heating element may be connected in series. The additional first temperature sensing element and the first temperature sensing element may be connected in series. The sensor may comprise an additional second temperature sensing element connected in series to the second temperature sensing element.

The heating elements may be connected in series and operated substantially at the same temperature.

The heating elements may be connected in series and the second temperature sensing elements may also be connected in series. The first temperature sensing elements may also be connected in series. In this case, a differential signal between the series combination of the first resistive temperature detectors and the second resistive temperature detector is obtained and used to determine the concentration of a fluid or particular fluid components based on different thermal conductivities. This allows the sensitivity of the sensor to be increased (by scaling up with the number of membranes, heating elements, and temperature sensing element) and also lowers the minimum resolution of the concentration of a particular gas component that can be sensed based on its difference in thermal conductivity compared to the rest of the fluid.

The heating element and the additional heating element may be configured to operate at different temperatures.

Each sensing element in combination with a corresponding first and second temperature sensing elements may operate independently and preferably at different temperatures to improve selectivity to different gases.

The heating element may be driven at more than one temperature, to increase the selectivity of the device. Gas thermal conductivity varies with temperature, and this variation is different dependent on the gas. In one drive mode, the heater can be driven at a temperature where the thermal conductivity of air and carbon dioxide are identical, and then used to detect another gas (e.g. hydrogen or methane). In this scenario, there will be known unwanted response from present carbon dioxide and thus the selectivity of the device is improved. The heater can also be run at the temperature that provides the optimum sensitivity for the gas that is being measured.

The fluid sensor may comprise an array of multiple dielectric membranes located over multiple etched portions of the semiconductor substrate, each membrane having: a heating element located within the dielectric membrane; a second resistive temperature detector element located in the proximity of the heating element and within the dielectric membrane. For each membrane of the array of membranes, the fluid sensor may comprise a first resistive temperature detector element located outside of the membrane and used as a reference. A differential signal may be measured between the at least one first resistive temperature detector element and the at least one second resistive temperature detector such that the differential signal is a function of the thermal conductivity of the fluid around the sensor and the concentration of particular fluid components with different thermal conductivities.

The array may contain one or several first resistive temperature detectors outside the dielectric membrane.

The fluid sensor may further comprise a covering located on a surface of the sensor, where the covering may comprise a hole configured to allow fluid travel from an outer surface of the covering to a fluid channel above the dielectric membrane.

The fluid sensor may further comprise a further temperature sensing element located outside the membrane region. The further temperature sensing element may be thermally isolated from the heating element.

An additional or further temperature sensor may be placed outside the dielectric membrane as a reference temperature sensing element to measure the ambient temperature or the temperature of the fluid, and the signal from the further temperature sensor may be used for temperature compensation for a more accurate calculation of the concentration of one or more specific components of the fluid.

The reference temperature sensing element (resistive temperature detector) could be used as part of a combination sensor (or a sensor fusion system) to read multiple physical properties of the environment (fluid composition and concentration of different components, fluid temperature or ambient temperature, or fluid velocity of fluid flow rate). Alternatively, a separate temperature sensor could be integrated on-chip as an extra resistive temperature detector, a diode or a transistor. An ambient temperature sensor could also be provided as part of the ASIC as a VPTAT or IPTAT sensor based on bandgap reference.

The temperature compensation can be done by using both the temperature reading from the additional temperature sensing element and the differential reading between the first and second resistive temperature sensors. This can be implemented by either a formula (within an algorithm) to adjust the final reading, or using a look up table and interpolation to determine the final reading.

The fluid sensor may further comprise an additional first temperature sensing element outside the membrane region and an additional second temperature sensing element located on or within the dielectric membrane region.

The fluid sensor may further comprise a pair of temperature sensing elements located on the dielectric membrane, wherein a first temperature sensing element of the pair of temperature sensing elements may be located on a first side of the heating element and a second temperature sensing element of the pair of temperature sensing elements may be located on a second side of the heating element.

The device is able to simultaneously sense properties of the fluid flow such as speed, mass, volume, shear stress as well as the composition of the flow (e.g., whether the fluid, in this case, the gas, has a certain $CO_2$ or hydrogen or methane percentage/ppm within air).

Therefore, the fluid sensor may comprise a first pair of sensing elements and a second pair of sensing elements, and a differential signal between the first pair of further sensing elements may be configured to measure a property of a composition of the flow (such as different components of the fluid and their concentrations based on their different thermal conductivities), and a differential signal between the second pair of sensing elements may be configured to measure a flow property (such as flow rate, flow direction, velocity or flow mass or flow volume rates).

The flow could be measured by employing the pair of temperature sensing elements displaced on either side of the heating element within the same dielectric membrane, and optionally used as a differential pair. The differential pair may be formed of one upstream sensing element and one downstream sensing element.

Holes or discontinuities (also referred to as recessed regions) may be placed so that they affect less the differential signal between the pair of temperature sensing elements that measure the properties of the flow but they affect significantly more the differential signal between the sensing elements that measure the composition of the flow.

According to a further aspect of the present disclosure, there is provided a fluid sensor for sensing a concentration or composition of a fluid, the sensor comprising: a semiconductor substrate comprising a first etched portion and a second etched portion, wherein the first etched portion and the second etched portion are substantially identical in size and shape; a dielectric region located on the semiconductor substrate, wherein the dielectric region comprises a first dielectric membrane located over the first etched portion of the semiconductor substrate and a second dielectric membrane located over the second etched portion of the semiconductor substrate; a single active heating element, wherein the active heating element is located only within the first dielectric membrane; a first temperature sensing element located within the second dielectric membrane; and a second temperature sensing element located on or within the first dielectric membrane, wherein the second temperature sensing element is substantially identical in shape and size to the first temperature sensing element, and wherein the separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

The first temperature sensing element may be placed on a second dielectric membrane wherein the second dielectric membrane does not comprise an active heating element. The two membranes may be located side by side, laterally spaced from each other, and may be identical in size and shape. The first temperature sensing element and the second temperature sensing element may be placed in a similar or identical position inside each of their respective dielectric membranes. Providing the temperature sensing elements in identical membranes improves matching characteristics.

The sensor comprises a single active heating element, wherein the active heating element is located only within the first dielectric membrane. Therefore, the sensor may comprise only one active heating element, such that there is no active heating element or electrically connected or powered heating element in the second dielectric membrane.

The second temperature sensing element may be a separate temperature sensing element, or the heating element may be configured to operate as the second temperature sensing element.

The sensor may further comprise an auxiliary structure located within the second dielectric membrane, and the auxiliary structure may be electrically isolated. The auxiliary structure may be configured such that the first dielectric membrane and the second dielectric membrane have the same mechanical and thermal stress properties.

Moreover, an auxiliary structure (also referred to as a dummy layer) (not connected electrically) may be located on or within the second dielectric membrane, such that the two temperature sensing elements have similar or identical structures in their proximity (i.e. neighbouring structures) and the two dielectric membranes with their respective embedded structures have substantially the same mechanical and thermal mass properties. The auxiliary structure may be electrically isolated, in other words the dummy structure in the second dielectric membrane may be not connected to any electrical signal. This provides the advantage that the two temperature sensing elements are very well matched (they are both on identical membranes, they have similar neighbouring structures around them) in terms of their characteristics, including stress, or deformations. Moreover, the two sensing elements see similar mechanical stress profile and therefore common mode effects such as ambient pressure or vibrations can be removed. Furthermore, the dynamic characteristics of the temperature sensing elements will be better matched because of their identical thermal mass.

According to a further aspect of the disclosure, there is provided a sensor assembly comprising the fluid sensor as described above and an application specific integrated circuit (ASIC) coupled to the sensor.

The control circuitry can be located on the same chip as the sensor (monolithically integrated), or can have an application specific integrated circuit (ASIC) coupled to the sensor. The ASIC can be on a separate chip, but within the same package, as a hybrid, co-packaged or using system in package (SIP) solutions. Alternatively, the ASIC could be placed outside the package, on a PCB (Printed Circuit Board) or within the same case/box.

The ASIC may be located underneath the sensor, for example using a die stack technique. Alternatively, the ASIC may be located side by side with the sensor or elsewhere. The ASIC may be connected to the sensor using wire bonding and pads, or using through-silicon-vias (TSV) extending through the semiconductor substrate. Alternatively, the sensor and the ASIC can be located on the surface of a common PCB or embedded in a PCB.

An ASIC may be provided within the same system or the same package or on-chip to provide electronic circuitry to drive, read-out signals and process signals from the sensor. The ASIC may be placed in a stack die configuration under the sensor and the sensor and ASIC are placed within a manifold or an open package, to allow contact to the fluid.

According to a further aspect of the disclosure, there is provided a sensor assembly comprising a sensor housing; and a fluid sensor as described above located within the flow sensor housing.

The fluid sensor housing may comprise an inlet and an outlet, and a fluid flow path for directing a fluid flow through the sensor. The sensor may be packaged within a packaging house or manifold with an inlet, outlet and a channel to provide more accurate measurements of the flow or the composition of the fluid.

According to a further aspect of the disclosure, there is provided a sensor assembly comprising the fluid sensor as described above, wherein the fluid sensor may be packaged on a printed circuit board in a flip-chip configuration.

The device may be packaged in a metal TO type package, in a ceramic, metal or plastic SMD (surface mount device) package. The device may also be packaged directly on a PCB, or with a flip-chip method. The device may also be embedded in a substrate, such as a customised version of one of the previously mentioned package, a rigid PCB, a semi-rigid PCB, flexible PCB, or any other substrate, in order to have the device surface flush with the substrate surface. The package can also be a chip or wafer level package, formed for example by wafer-bonding.

In particular, the package may be designed such that there is a surface very close to the membrane, for example in a flip-chip scenario, such that the surface is less than 50 um from the membrane. This increases the power loss through the fluid and improves the sensitivity of the sensor.

According to a further aspect of the disclosure, there is provided a method of measuring a concentration or composition of a fluid using a fluid sensor as described above, the method comprising: applying an electrical bias to the heating element; and monitoring the electrical bias applied to the heating element and using the value of the electrical bias applied to the heating element and the differential signal to determine the concentration or composition of the fluid based on thermal conductivity of the fluid.

Applying an electrical bias to the heating element may comprise applying an electrical bias such that the differential signal between the first temperature sensing element and the second temperature sensing element may be minimised. Minimised may refer to reducing the differential signal to zero or substantially zero.

The electrical power, current, or voltage applied to the heating element may be adjusted to bring to zero or substantially zero the differential signal between the first and second temperature detector elements (by varying the heating element power, current, or voltage could be such that the resistances of the two temperature detectors or the voltages across the temperature detectors are equal). This may be done during the calibration of the sensor or during the operation of the sensor. This could be set as calibrated point, giving a zero differential signal. Alternatively, this could be set during the operation and the heater power/current/voltage could be measured as an indication of the fluid compositions or the concentration of its components The change in the electrical power, voltage or current through the heater may be monitored to measure one or more concentrations of specific components of the fluid based on their different thermal conductivities.

The first and second temperature sensing elements, and optionally the heating element, may be connected to a differential amplifier or a Wheatstone bridge type circuit such that the differential signal may be used to measure one or more concentrations of specific components of the fluid based on their different thermal conductivities.

The measurement of the differential signal (for example, the differential resistance) can be performed in a number of ways. A first way is to apply a constant current to both the first and second temperature sensing elements (temperature resistive detectors) and measure the voltage difference between them using a differential amplifier. A further method is to use a Wheatstone bridge or other type of bridges. For both these methods, a calibration can be done initially to set a zero point value. This can either set a differential voltage value when the target fluid (or component of the target fluid) is not present, or modify the current to one of the resistors to ensure the differential voltage is at zero when the target fluid is not present. Alternatively, the calibration can be done initially to set a zero point value of the differential signal when the component of the fluid (e.g. $CO_2$) is known (e.g. 400 ppm of $CO_2$ in air) by using an external precision CO2 device (e.g. NDIR sensor).

The method may comprise driving the heating element in pulse mode or AC mode to modulate the temperature of the heating element to vary the differential signal; and using the differential signal to selectively differentiate between different fluid components and/or determine the concentration of the different components.

The temperature of the heating element may be modulated by varying the current, voltage or power to different levels and/or with different electrical pulses such as to vary the differential signal between the first and second resistive temperature detectors in order to selectively differentiate between different fluid components and/or to provide information regarding the concentration of such components.

The temperature of the heater may be modulated and the voltage difference between the first and second temperature sensing elements at different temperatures may be assessed against reference values, and the difference between the two may be indicative of the flow composition.

The heating element temperature may be modulated by applying different power levels to increase sensitivity and selectivity to different fluid components based on their thermal conductivity variation with temperature. For example, the difference between the thermal conductivities of $CO_2$ and the air is higher at room temperature than at high temperatures. The opposite is true for Methane, so the difference between the thermal conductivities of methane and the air is lower at room temperature than at high temperatures. Hydrogen has also a different variation of the thermal conductivity with temperature than that of $CO_2$ or air. By running the heater at different temperature levels (i.e. modulating the temperature of the heater), it is entirely possible to differentiate between the contributions of different concentrations of fluid components in the fluid. In this way, for example, Hydrogen and $CO_2$ contributions can be decoupled and their concentration values can be found.

The heater (also referred to as the heating element) may be operated in a pulse mode (e.g. driven with a square wave, sinusoidal wave, Pulse Width Modulated wave (PWM), Pulse Density Modulation, etc.) or continuous mode. The pulse mode has, among others, the advantage of reduced power consumption, reduced electromigration for enhanced device reliability/lifetime, and improved fluid properties sensing capabilities. Pulses could be used in different polarities to further reduce the impact of electromigration on the heating element.

Different drive modes and measurement modes are possible. For example, the heater can be driven using PWM, and the off time of the PWM can be used to measure heater resistance, and/or differential signal. This measurement can be done in a very short time, faster than the thermal time constant of the membrane to avoid self-heating.

Selectively differentiating between different fluid components and/or determining the concentration of the different components may comprise using a neural network.

An algorithm containing machine learning and artificial intelligence may be implemented. For example, the sensor or a fluid sensing system may further comprise a controller or a processing system comprising a neural network. The neural network may be trained using data from different known gases or mixture of gases at different temperatures. The use of a trained neural network to identify known gases or a mixture of gases can improve accuracy, sensitivity and selectivity of the fluid sensor.

The neural network may be trained to recognise the composition of a gas mixture based on the differential signal between the first and second temperature sensing elements. The neural network could be trained using supervised learning based on a set of data of sensor output values for known gas mixtures at a set of heating element temperatures. The inputs to the neural network could be the sensor output values at a predetermined set of temperatures. The neural network may be configured to process each differential signal from the first and second temperature sensing elements in order to determine the components of the gas mixture and the concentrations of each component in the gas mixture. The outputs from the neural network could be the fraction of each gas in the mixture. Synthetic training data could be generated to enhance the training by providing, for example, many more combinations of gases than would be practically realisable in a real laboratory. A support-vector machine could be trained to discriminate between different gases.

The method may comprise: applying a modulated function to the heating element, the first temperature sensing element, or the second temperature sensing element; measuring the modulation, the time delay, or the phase shift of the differential signal between the first temperature sensing element and the second temperature sensing element; and determining a concentration or composition of the fluid using the measured modulation, time delay or phase shift.

A transient, modulated, or pulsed signal may be applied to either the heater element or the first or second temperature sensing elements, and the signals from the first or second temperature detectors will consequently be transient, and their time shape, time delay, or phase shift depends on both the thermal conductivity and the thermal diffusivity of the fluid around the sensor and its concentration of particular fluid components with different thermal conductivities and the thermal diffusivities The heaters or the first or second resistive temperature detectors can be biased with a transient signal (e.g. AC, square wave, pulsed, step). Using transient based signals, the thermal diffusivity can be determined using the measured values from the first and second temperature sensing elements. In this way, more information can be extracted from the environment.

In a method of transient fluid sensor drive modes, a step change in input current can be applied to the heater and the time constant for the temperature rise in the heater can be measured. This time constant can give information about the thermal conductivity and diffusivity of the environment. Both can be used to identify gas concentration.

In another method of transient sensor drive modes, a sinusoidal wave can be applied to the heater. The change in amplitude and change in phase shift can provide information on thermal conductivity and thermal diffusivity, thus providing information on the gas concentration.

Any of the resistive temperature detectors may be driven in short pulses of power, voltage or current. The temperature sensing elements (resistive temperature detectors) may be driven in a pulse mode (e.g. driven with a square wave, sinusoidal wave, Pulse Width Modulated wave, Pulse Density Modulation, etc.) or continuous mode. The pulse mode has, among others, the advantage of reduced self-heating of the temperature sensing elements, which minimises the noise and increases the sensitivity or the signal to noise ratio. This is particularly important for the second sensing temperature element (which is closer to the heating element), which suffers more from the self-heating effect than the first temperature element. This however could also be important for the first temperature sensor, especially if the first temperature sensor is placed on a dielectric membrane (the same membrane as the heating element and the second temperature sensing element, or a different membrane).

Whilst several methods are described, any other method of driving the sensor that can provide information on the environment that is being measured may be used.

According to a further aspect of the present disclosure, there is provided a fluid sensing system comprising a fluid sensor as described above; and a controller configured to perform a method as described above.

The fluid sensing system may include a hardware or software interface wherein an algorithm is implemented to facilitate to selectively differentiate between different fluid components and/or to provide information regarding the concentration of such components.

A software algorithm configured to perform any of the methods as described above could be implemented to differentiate between these components and increase sensitivity related to each of the components of the fluids. The software algorithm could be implemented in a local microprocessor. Calibrated data could be stored in a memory device or integrated circuit. Alternatively, the software could be incorporated within an ASIC and driving of the sensor and processing of the signal could be done within an ASIC.

Processing of the signal could also be done remotely in a sensor hub, or on an external server accessed using the Internet (for example, the cloud).

Sampling and averaging of the data, as well as ways to remove outliers from the data could also be used as part of an algorithm and could be implemented in hardware using different electronic components such as micro-controllers, memories or could be done using an ASIC.

Readings from the sensor may be averaged in several ways, for example using a moving mean average or a moving median average. A moving mean average is useful for removing random noise from the signal. A moving median average is useful for removing outliers.

According to a further aspect of the present disclosure, there is provided a method of manufacturing a fluid sensor as described above, the method comprising: forming a first dielectric membrane located over a first etched portion of a semiconductor substrate semiconductor substrate comprising a first etched portion; forming a heating element located within the first dielectric membrane; forming a first temperature sensing element spatially separated from the heating element, wherein the first temperature sensing element is located outside of the first dielectric membrane and over the semiconductor substrate, or wherein the first temperature sensing element is located on or within the first dielectric membrane and wherein the fluid sensor comprises at least one recessed region within the first dielectric membrane configured to thermally isolate the heating element from the first temperature sensing element.

BRIEF DESCRIPTION OF THE FIGURES

Some embodiments of the disclosure will now be described by way of example only and with reference to the accompanying drawings, in which.

DETAILED DESCRIPTION OF THE PREFERRED EMBODIMENTS

Some examples of the disclosed device are given in the accompanying figures.

Figure 1:
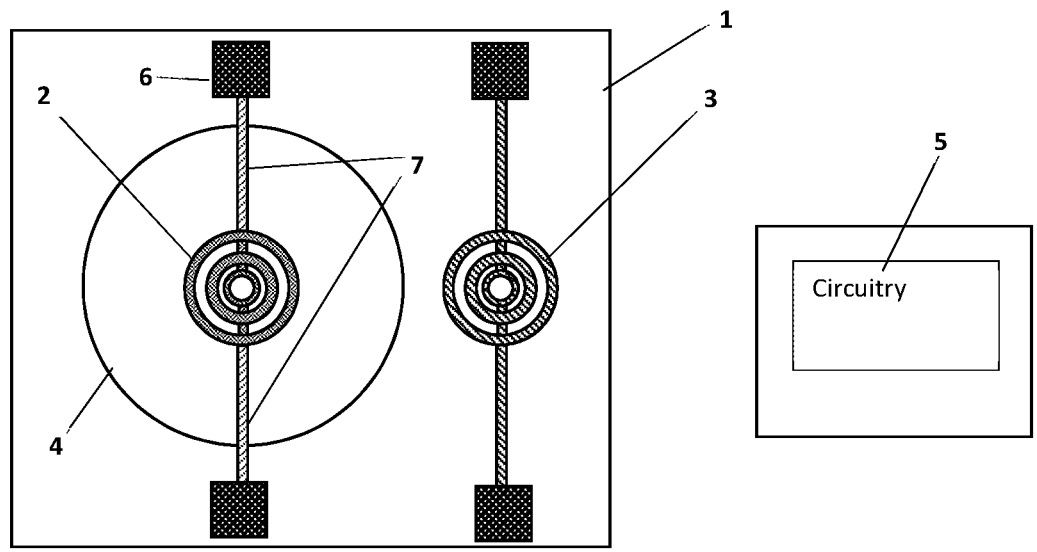
FIG. 1 shows a top view of a thermal conductivity fluid sensor with one circular resistor within a membrane, and one circular resistor outside the membrane, and circuitry to control & measure the sensor.

FIG. 1 shows a top view of a thermal conductivity fluid sensor. It comprises a chip 1 made of a semiconductor substrate and a dielectric layer or region suspended on or over an etched portion of the semiconductor substrate, defining a region of the dielectric layer above the etched portion as a dielectric membrane 4. There is a resistor 2 embedded within the membrane, and track 7 connect it to bond pads 6. The resistor 2 is configured to operate as a heating element 2, and in this embodiment, it also acts as a resistive temperature detector element. There is another temperature detector element (also referred to as a thermal detector element) 3 outside the dielectric membrane. The fluid sensor also includes circuitry 5, that uses a differential signal from the two temperature detector elements 2, 3 to determine the composition of the fluid based on its thermal conductivity.

Due to the spatial separation between the heating element 2 and the first temperature sensing element 3, the heater 2 operates at a higher temperature than the first temperature sensing element 3 even in zero flow (or when no flow is present) when the heater 3 is powered up. The temperature of the first temperature sensing element 3 is dependent on the ambient temperature, and the temperature of the heating element 2 can vary depending on the heat loss to the surrounding fluid—which is dependent on the thermal conductivity of the fluid. The temperature differential (differential signal) between the heating element 2 and the first temperature sensing element 3 may be proportional to the concentration of a fluid.

For example, if $CO_2$ is present in the sensor, the thermal conductivity of the $CO_2$ is smaller than that of air, the temperature difference between the heater 2 and the first temperature sensing element 3 will be greater as the thermal conductivity of the $CO_2$ is smaller than that of air.

The temperature difference between the heating resistor 2 and the first temperature sensing element 3 could be translated into a voltage difference or resistance difference, depending on the temperature sensing element employed. For diodes supplied with constant current, or for thermopiles, the voltage difference is appropriate. For Resistive Temperature Detectors (RTD), several read-out techniques could be employed such as using instrumentation bridges to measure change in the resistance or using current mirrors and sensing the voltage difference.

In this figure, the membrane is shown as circular. However, it can be rectangular, rectangular with rounded corners or any other shape. Similarly the resistors 2 and 3 are shown as circular, but can be any shape including ring, meander or rectangular. The resistor may be made of a CMOS metal such as aluminium, tungsten, titanium or copper, or a non-CMOS metal such as gold or platinum, or from polysilicon or single crystal silicon.

Figure 2:
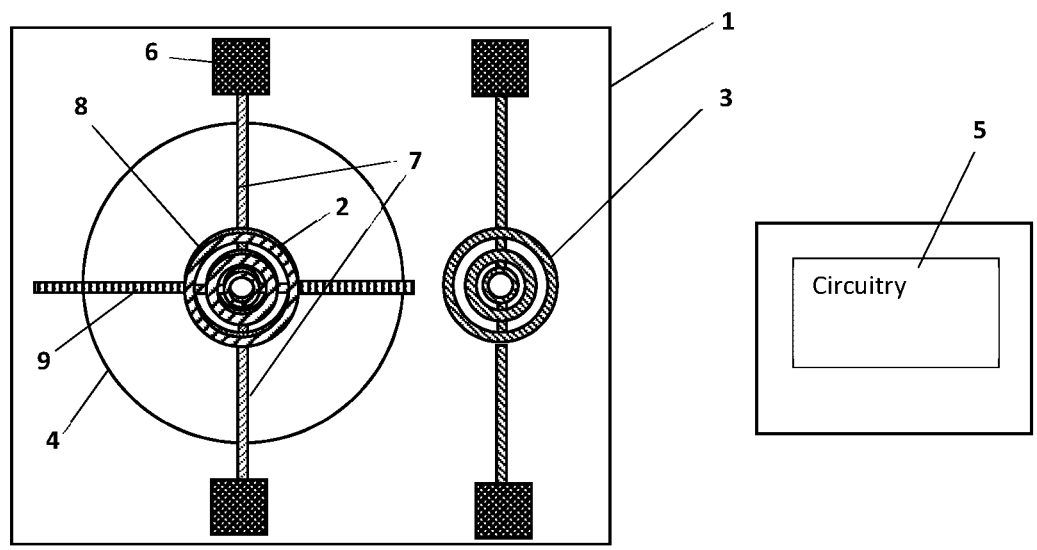
FIG. 2 shows a top view of a thermal conductivity fluid sensor with two circular resistors within the membrane.
Figure 3:
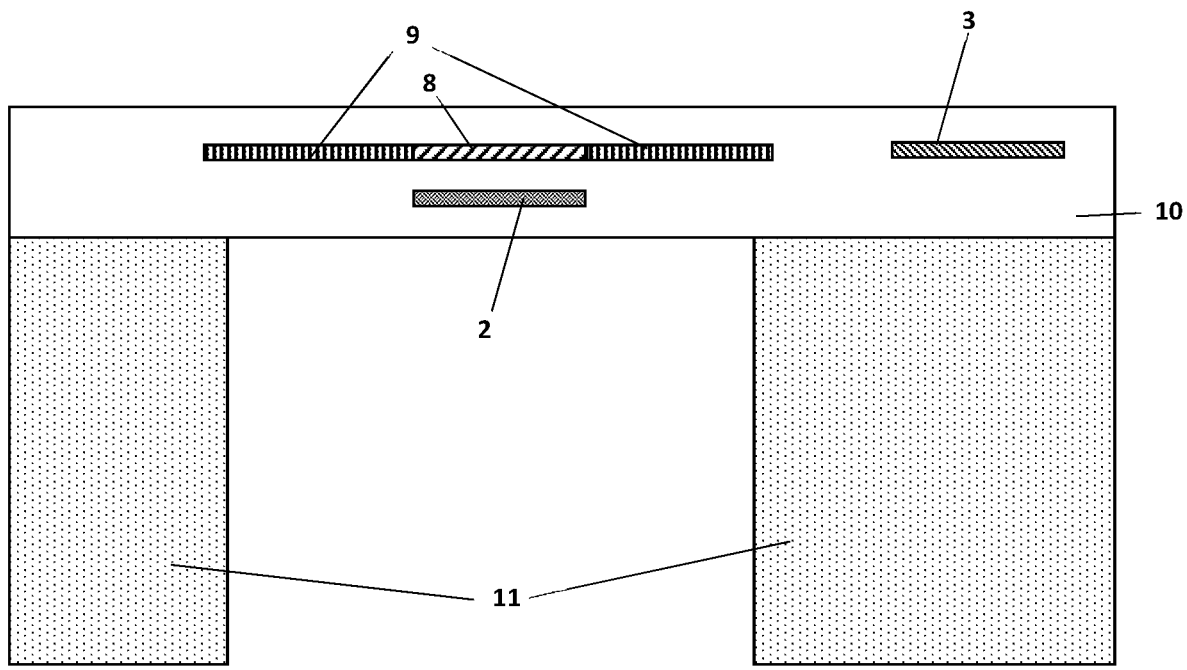
FIG. 3 shows the cross-section of a thermal conductivity fluid sensor shown in FIG. 2.

FIG. 2 shows a top view of an alternative thermal conductivity fluid sensor, and FIG. 3 illustrates a cross-section of the sensor of FIG. 2.

The thermal conductivity fluid sensor of FIGS. 2 and 3 has two circular resistors 2, 8 within the membrane region 4. One of the resistors is configured to operate as a heater element 2, and the other resistor within the dielectric membrane is configured to operate as temperature detector element 8. As shown in FIG. 3, the two resistors 2, 8 are made of different layers within the dielectric layer 10 and can be in close proximity to each other so that they are at substantially the same temperature. The substrate 11 is a semiconductor and the resistive temperature detectors are embedded within the dielectric layer 10.

Due to the spatial separation between the heating element 2 and the second temperature sensing element 8 (both on or within the dielectric membrane 4) and the first temperature sensing element 3, the second temperature sensing element 8 operates at a higher temperature than the first temperature sensing element 3 even in zero flow (or when no flow is present) when the heater 2 is powered up.

Figure 4:
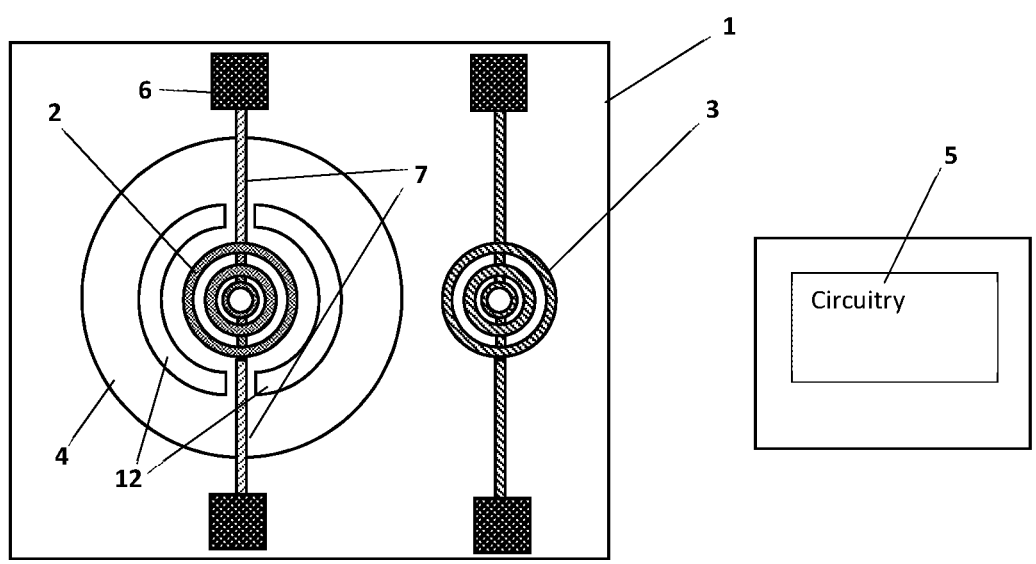
FIG. 4 shows the top view of a thermal conductivity fluid sensor with recessed regions formed of slots within the membrane.
Figure 5:
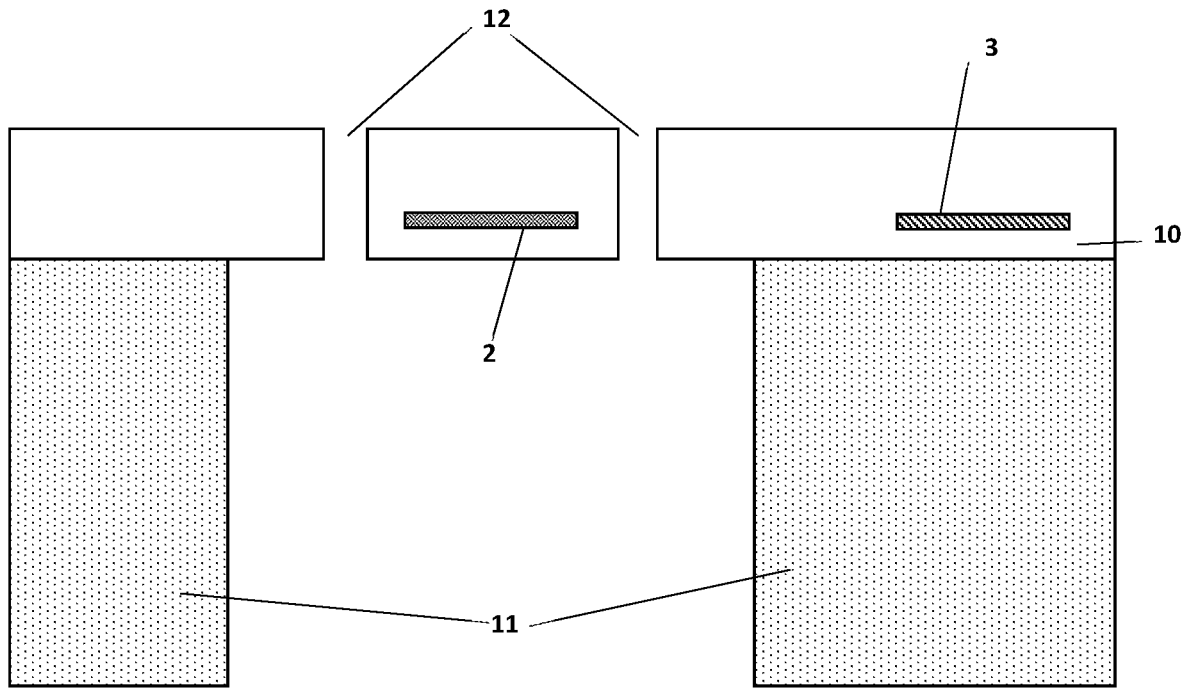
FIG. 5 shows the cross-section of a thermal conductivity fluid sensor with slots in the membrane, as shown in FIG. 4.

FIG. 4 shows a top view of an alternative thermal conductivity fluid sensor, and FIG. 5 illustrates a cross section of the sensor of FIG. 4.

The thermal conductivity fluid sensor of FIGS. 4 and 5 has a circular resistive heater 2 acting as both a heater element and a temperature detector element, and has two recessed regions within the membrane, which are shown as two slots 12. The slots are circular around the heater.

The recessed regions minimise the thermal path through the solid dielectric membrane, forcing more heat to dissipate via convection and conduction through the environment (mostly above the membrane via conduction and convection), but partly also via heat conduction through the space formed by the slots or below the membrane. In this way a larger proportion of the heat loss of the heating element is to the surrounding fluid. So when there is a change in the thermal conductivity of the fluid the change in temperatures of the heating element and the second temperature sensing element are increased—thus the recessed regions increase the sensitivity of the device.

The presence of the slots also helps to reduce the power consumption of the device (for the same heater temperature), because of the reduction in the total heat losses. Furthermore, the slots help to reduce the thermal response time (increase the speed at which the heater heats up when supplied with an electrical power pulse) due to the decrease in the thermal mass of the membrane.

Figure 6:
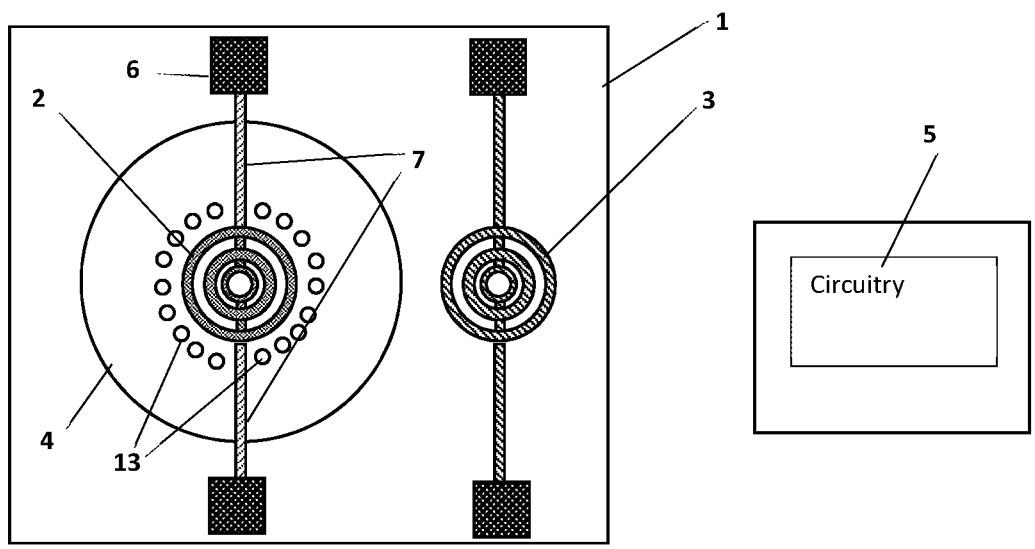
FIG. 6 shows the top view of a thermal conductivity fluid sensor with recessed regions formed of arrays of circular holes.

FIG. 6 shows a top view of a thermal conductivity fluid sensor with a circular resistive heater 2 acting as both a heater element and a temperature detector element, and several recessed regions around the resistor in the shape of small circular holes 13. Similar to the slots of FIGS. 4 and 5, the circular holes 13 increase the proportion of power loss to the fluid and there improve sensitivity, reduce thermal response time and power consumption.

Figure 7:
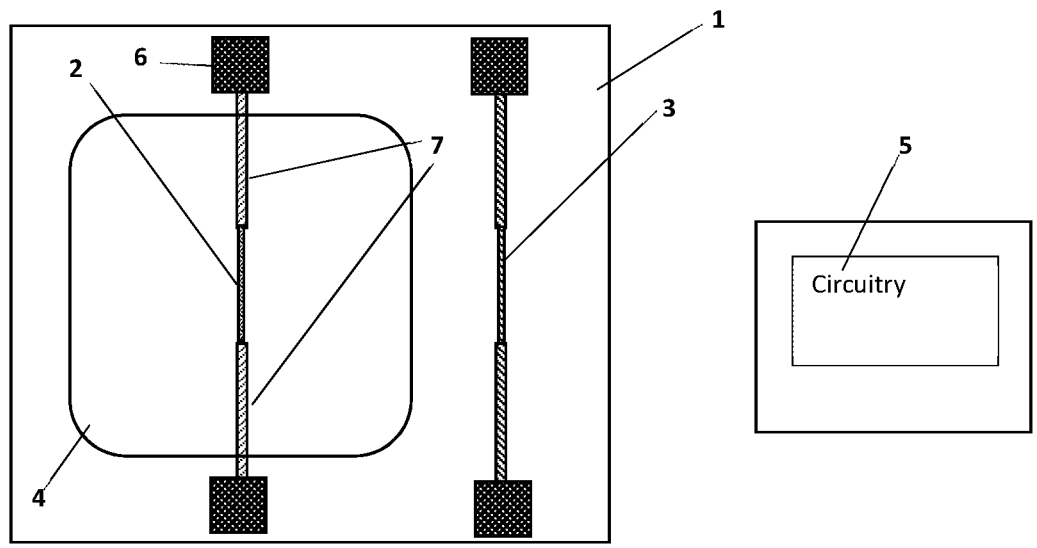
FIG. 7 shows the top view of a thermal conductivity sensor fluid with one wire resistive temperature detector within a membrane, and one wire resistor outside the membrane.

FIG. 7 shows a top view of a thermal conductivity sensor with a wire shaped resistor 2 within the membrane region, and one wire shaped resistor outside the membrane 3, with the resistor within the membrane 2 acting as both a heater element and as a first temperature detector element. The membrane 4 is in case is a rectangular membrane with rounded corners—but can also be of any other shape. This sensor operates similarly to the sensor of FIG. 1.

Figure 8:
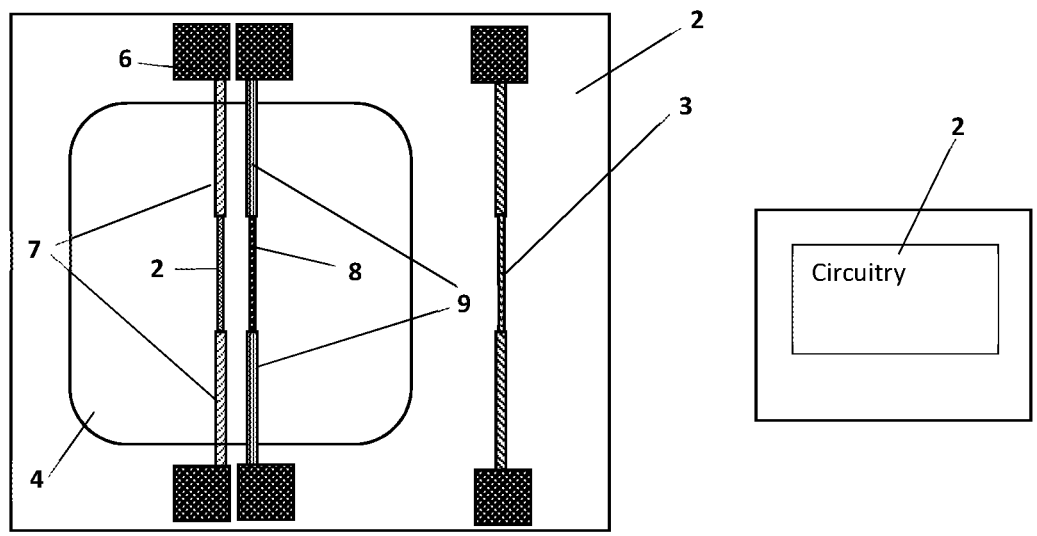
FIG. 8 shows the top view of a thermal conductivity fluid sensor with two wire resistive temperature detectors within a membrane.

FIG. 8 shows a top view of a thermal conductivity sensor with two wire resistors within the membrane region, with one operating as a heater element 2, and the other operating as a temperature detector element 8.

FIGS. 9(a) to 9(d) each show a top view of an alternative thermal conductivity fluid sensor with recessed region 12 within the dielectric membrane. Recessed regions reduce the thermal losses from the heater, and increase the percentage of power loss to the fluid, thus improving the device sensitivity.

Figure 9A:
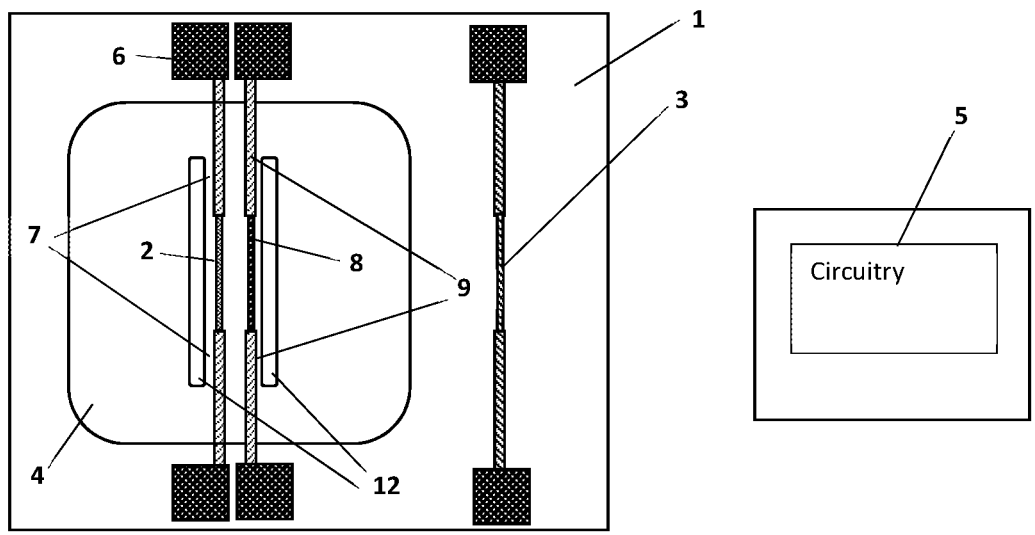
FIG. 9(a) shows the top view of a thermal conductivity fluid sensor with two wire resistive temperature detectors within a membrane and recessed regions shaped as slots.

FIG. 9a shows sensor where the heater element 2 is a wire resistor, and a second thermal detector element 8 is also a wire resistor.

Figure 10A:
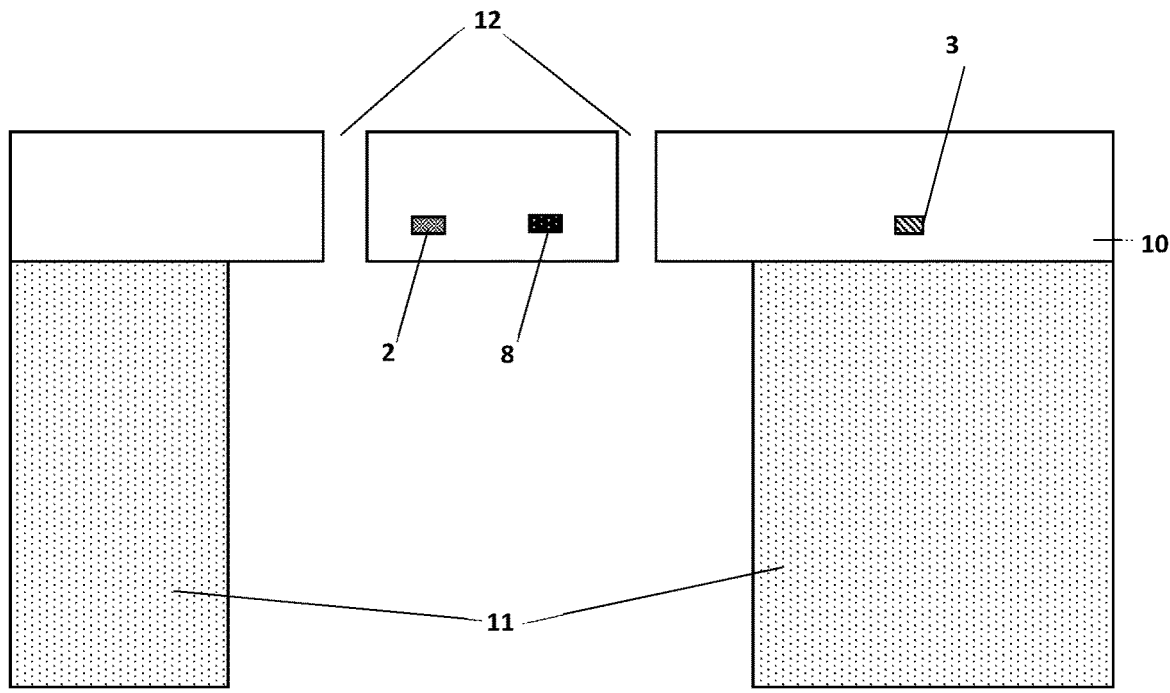
FIG. 10(a) shows the cross-section of the device in FIG. 9(a)

FIG. 10a shows the cross-section of the device in FIG. 9a. There are two wire resistors, one as a heater element 2, and one as a first thermal detector element 8.

Figure 9B:
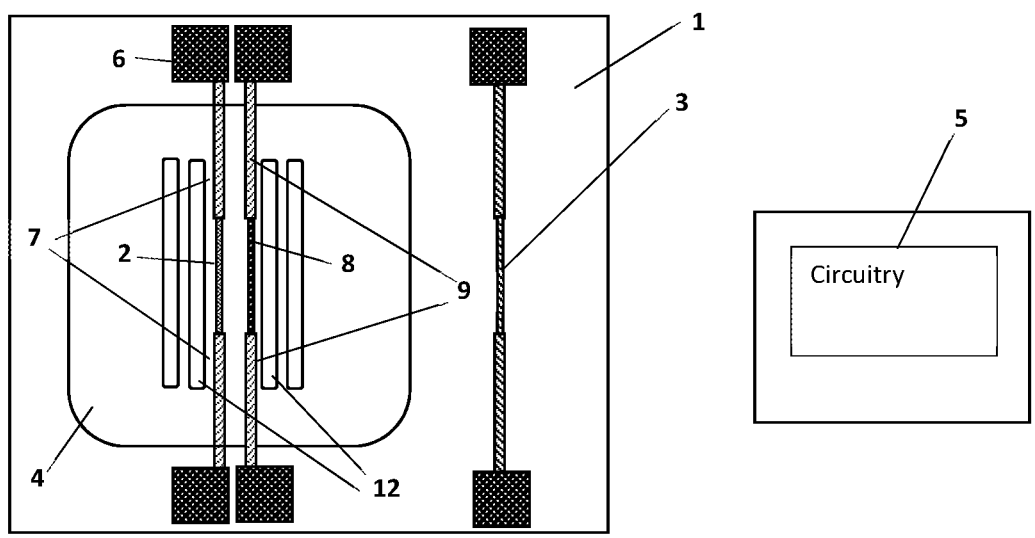
FIG. 9(b) shows an alternative thermal conductivity fluid sensor with a greater number of recessed regions within the dielectric membrane.

FIG. 9b shows a sensor where there are four recessed regions 12 on the membrane, two on either side of the heater and second temperature detector element. By increasing the number of recessed regions, the sensitivity of the device is increased.

Figure 9C:
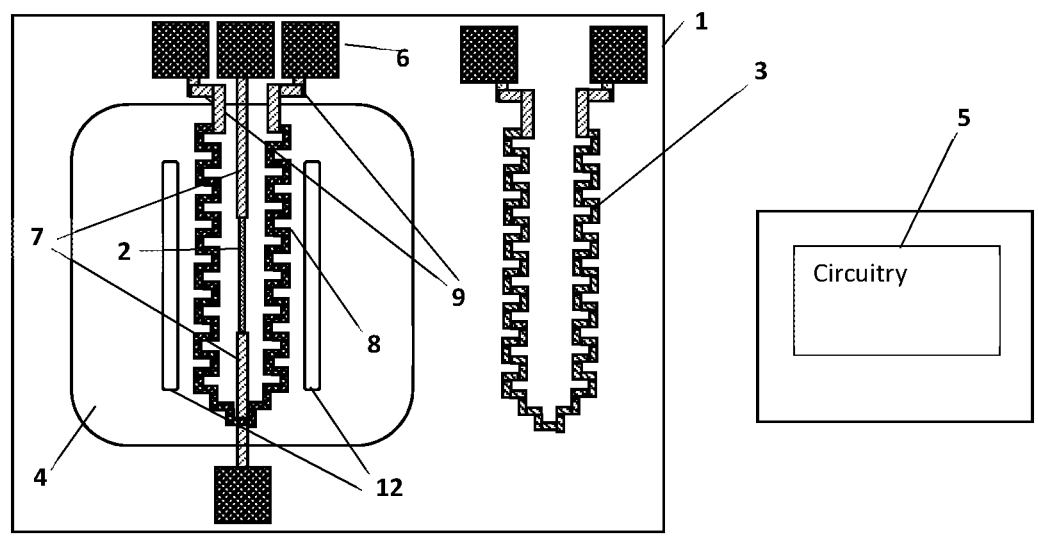
FIG. 9(c) shows an alternative thermal conductivity fluid sensor having a resistive wire having a meander shape within the same layer as the heater.

In FIG. 9c, the second thermal detector element 8 has a meander shape and is designed such that it is located on both sides of the heater 2. In this configuration, the second thermal detector element 8 is located in a different layer of the dielectric layer than the heater 2. The shape of the first temperature sensing element 3 is also the same as the second temperature sensing element 8.

Figure 10B:
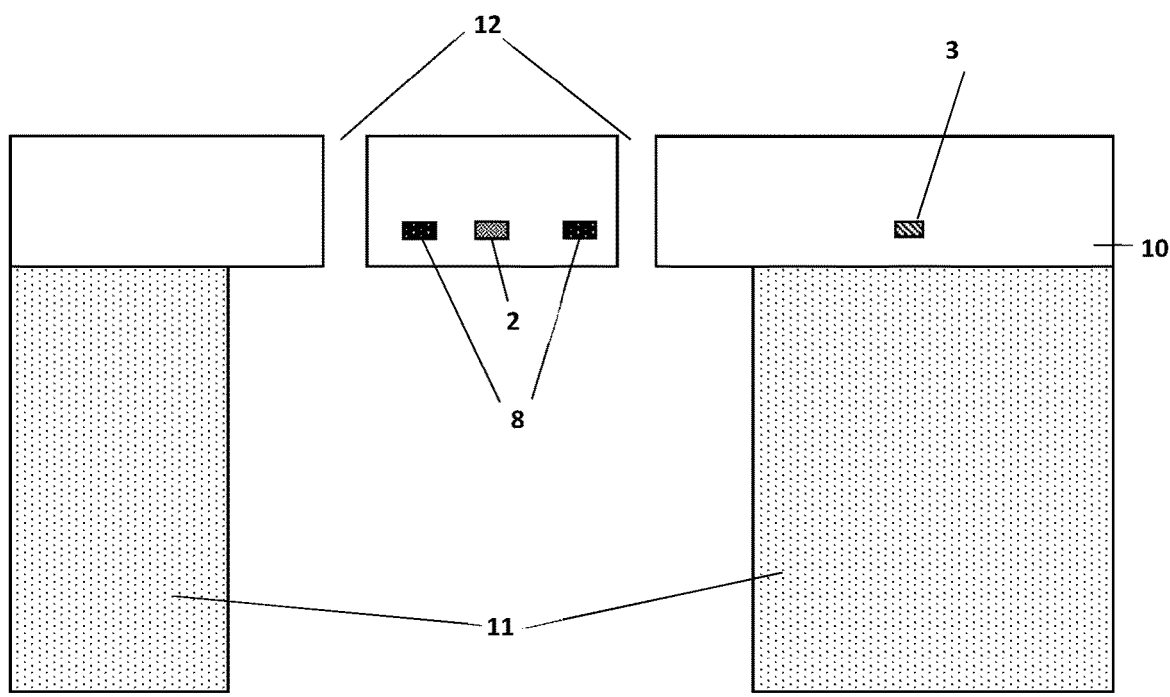
FIG. 10(b) shows the cross-section of the device in FIG. 9(c)

FIG. 10b shows the cross-section of the device in FIG. 9c. The first thermal detector element 8 is in two parts, and split either side of the heater.

Figure 9D:
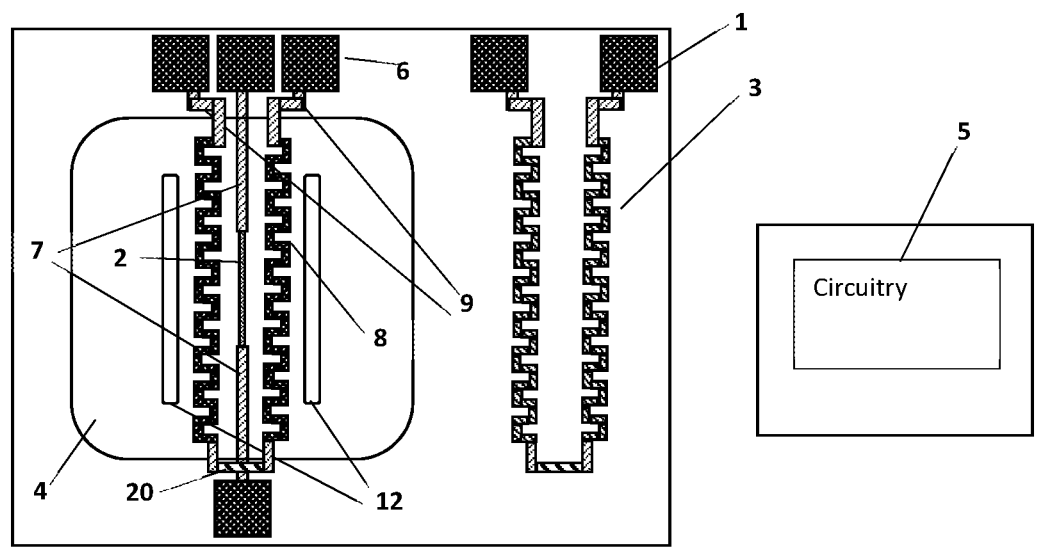
FIG. 9(d) shows an alternative thermal conductivity fluid sensor having a wire having a meander shape and a connecting element connecting two portions of the wire.

FIG. 9d shows a sensor in which the second thermal detector element 8 also has a meander shape and is located on both sides of the heater 2. The second temperature detecting element 8 is formed of two portions, with a first portion of the second temperature detecting element 8 located on a first side of the heating element 2, and a second portion of second temperature detecting element 8 located on a second, opposite side of the heating element. A connection between the two portions of the second temperature detecting element is located outside the dielectric membrane 4, and is formed of a connecting element 20. This allows the first thermal detector element 8 to be made within the same layer of the dielectric layer as the heater element 2, with only the connecting element 20 located within a different layer of the dielectric region, and used to bridge the two portions of the second thermal detector element 8. The shape of the first temperature sensing element 3 is also the same as the second temperature sensing element 8.

Figure 11:
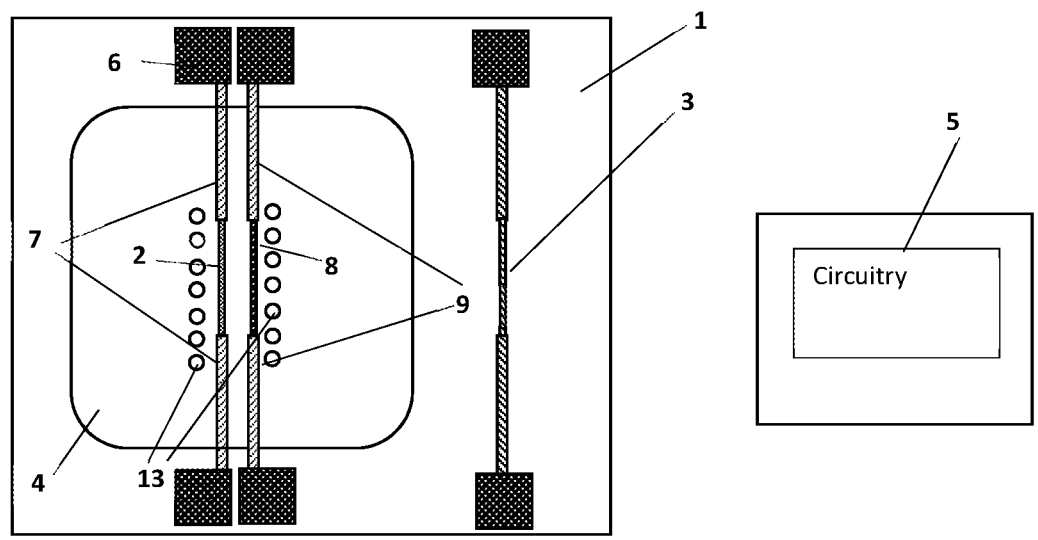
FIG. 11 shows the top view of a thermal conductivity fluid sensor with two wire resistive temperature detectors within a membrane, and recessed regions comprising arrays of circular holes.

FIG. 11 shows a top view of a thermal conductivity fluid sensor with a recessed region 13 including arrays of circular holes within the dielectric membrane region 4.

Figure 12A:
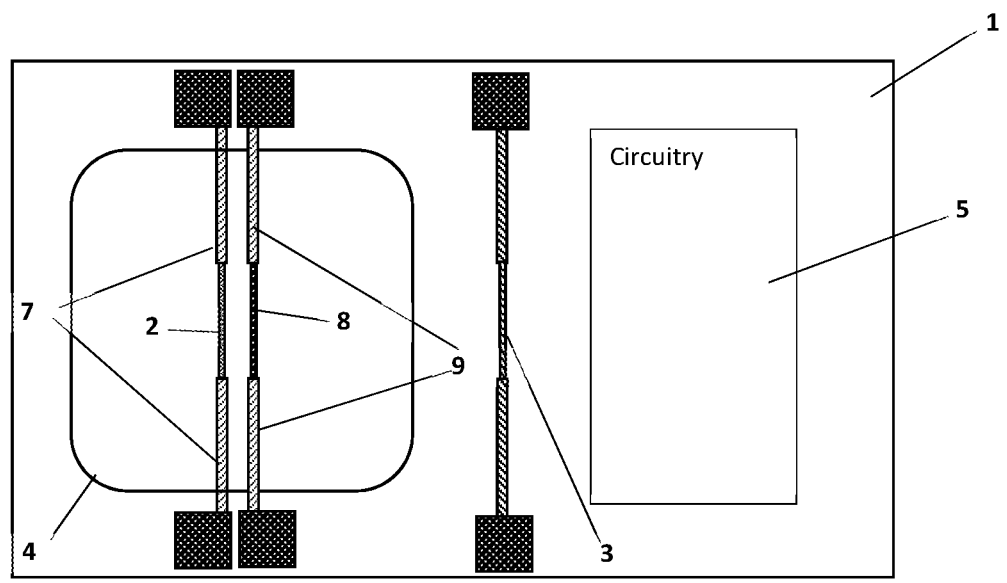
FIG. 12(a) shows the top view of a thermal conductivity fluid sensor with the circuitry on the same chip.

FIG. 12(a) shows a top view of a thermal conductivity fluid sensor with circuitry 5 located on the same chip as the heating element 2, and the first and second temperature sensing elements 3, 8. The circuitry 5 is used to control and drive the heater 2, and also measure the differential signal between the first temperature detector element 3 and the second temperature detector element 8. It may comprise a constant current or constant resistor drive circuit, a constant current source, a Wheatstone bridge, an amplifier, an Analog to Digital convertor, a Digital to Analog Convertor and/or a microcontroller.

Figure 12B:
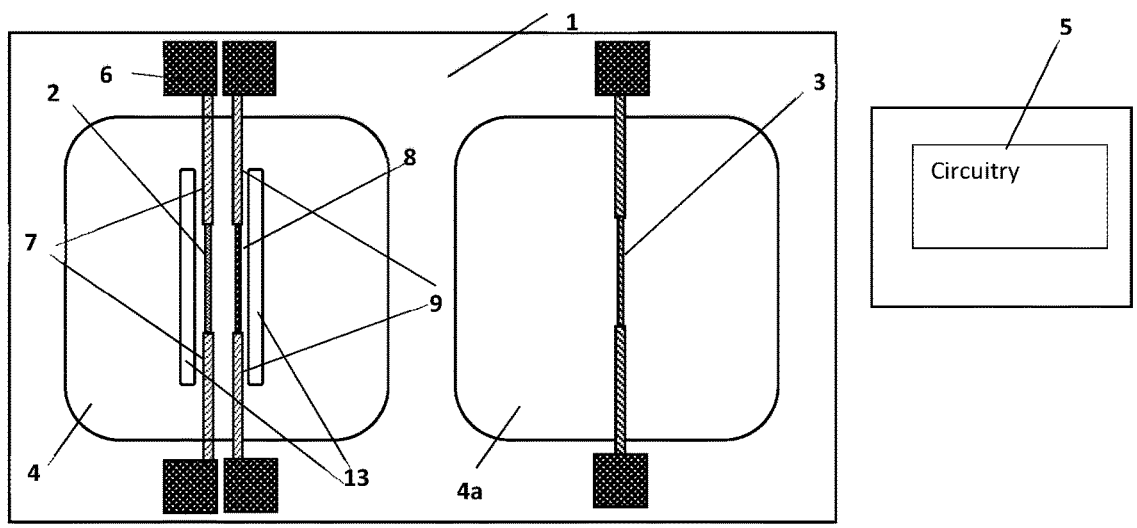
FIG. 12(b) shows the top view of an alternative thermal conductivity fluid sensor, where the first temperature sensing element is placed on a second dielectric membrane.

FIG. 12(b) shows a top view of a further fluid sensor where the first temperature sensing element 3 is on a second membrane, 4a, separate and identical in dimensions with the first membrane 4. The second dielectric membrane 4a has no active heating element. Common mode effects such as extra temperature rise due to self-heating when the two temperature sensing elements are biased can be removed. The effect of pressure and/or residual stress/strain in the membranes can also be cancelled out. Finally, the thermal mass associated with the two temperature sensing elements can be identical (or very similar) and thus dynamic mismatching effects can be minimised.

Figure 12C:
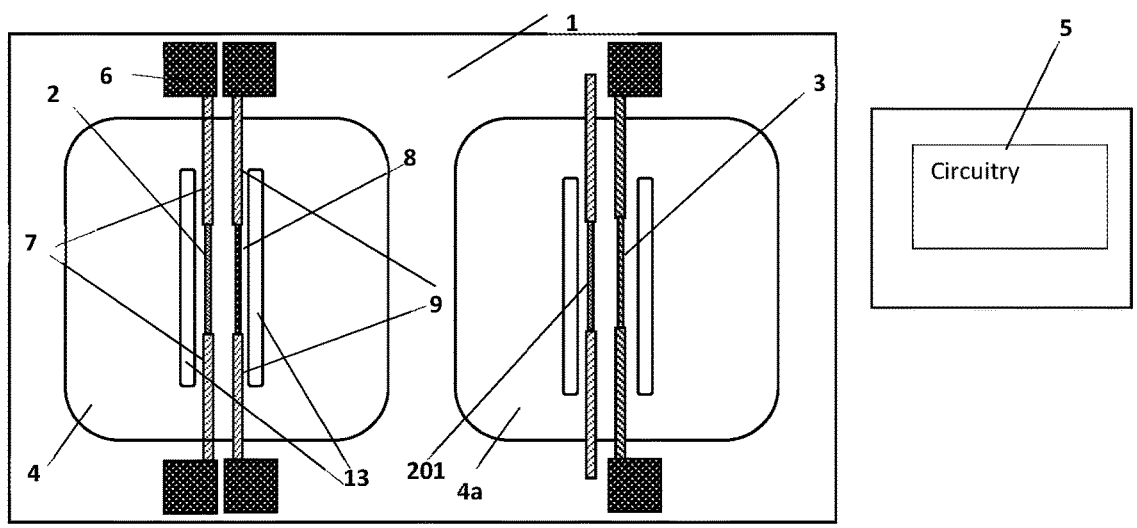
FIG. 12(c) shows the top view of an alternative thermal conductivity fluid sensor, where the first temperature sensing element is placed on a second dielectric membrane, having a dummy element.

FIG. 12(c) shows a similar fluid sensor to the one shown in FIG. 12(b). Here an auxiliary structure 201 including one or more further dummy layers or elements is located on or within the second dielectric membrane 4a, such that the two temperature sensing elements have similar structures in their proximity (i.e. neighbouring structures) and the two membranes with their respective embedded structures seem to be identical from a mechanical and thermal mass perspective. For example, the auxiliary structure 201 may have identical size, shape and materials as the heating element 2. However, the dummy elements 201 in the second membrane are not connected to any electrical signal, and are therefore electrically isolated. The advantage of this fluid sensor is that the two temperature sensing elements 3, 8 are very well matched (they are both on identical membranes, they have similar neighbouring structures around them) in terms of their characteristics, including stress, or deformations. Moreover, the two sensing elements see similar mechanical stress profile and therefore common mode effects such as ambient pressure or vibrations can be removed.

Figure 13:
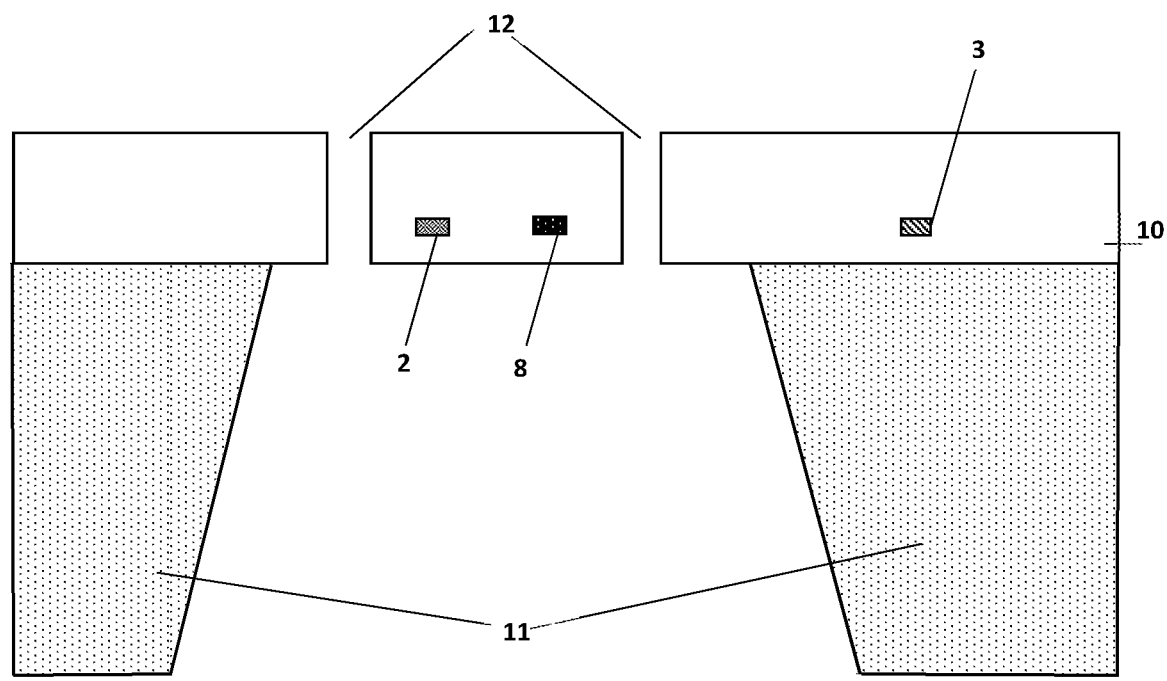
FIG. 13 shows the cross-section of a thermal conductivity fluid sensor with sloping sidewalls of the etched semiconductor substrate.
Figure 14A:
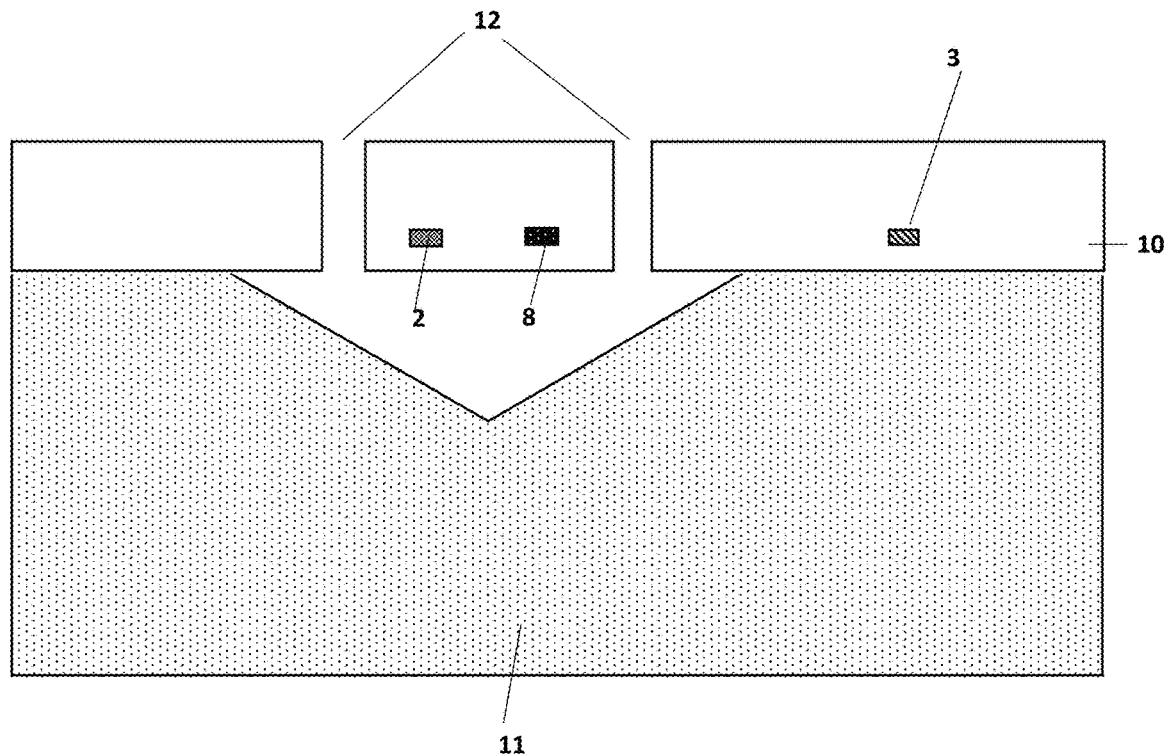
FIGS. 14(a), 14(b), and 14(c) show cross-sections of alternative thermal conductivity fluid sensors where the etched portion of the substrate does not extend through the entire thickness of the substrate.
Figure 14B:
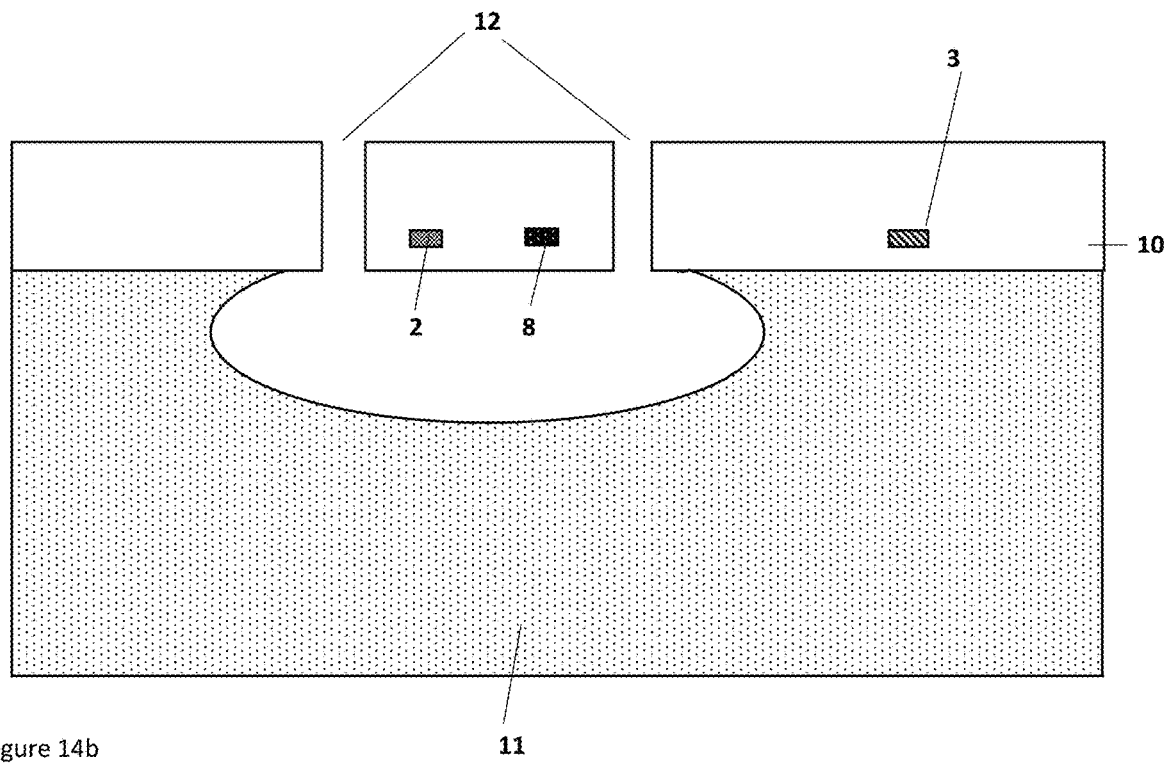

FIGS. 13, 14(a), and 14(b) show etched regions within the semiconductor substrate 11 a thermal conductivity fluid sensor. In FIG. 13, the etched region has sloping sidewalls, which can be achieved by use of KOH or TMAH etching. Such an etching method is cheaper, but requires a larger chip area.

FIGS. 14(a) and 14(b) show thermal conductivity fluid sensors where the etched region does not extend through the entire semiconductor substrate 11. This can be achieved by etching from the front side of the substrate. This process results in a membrane or bridge structure supported by a dielectric beam. This results in a sensor with lower thermal power losses, but also with lower mechanical robustness compared to the sensor of FIG. 13.

Figure 14C:
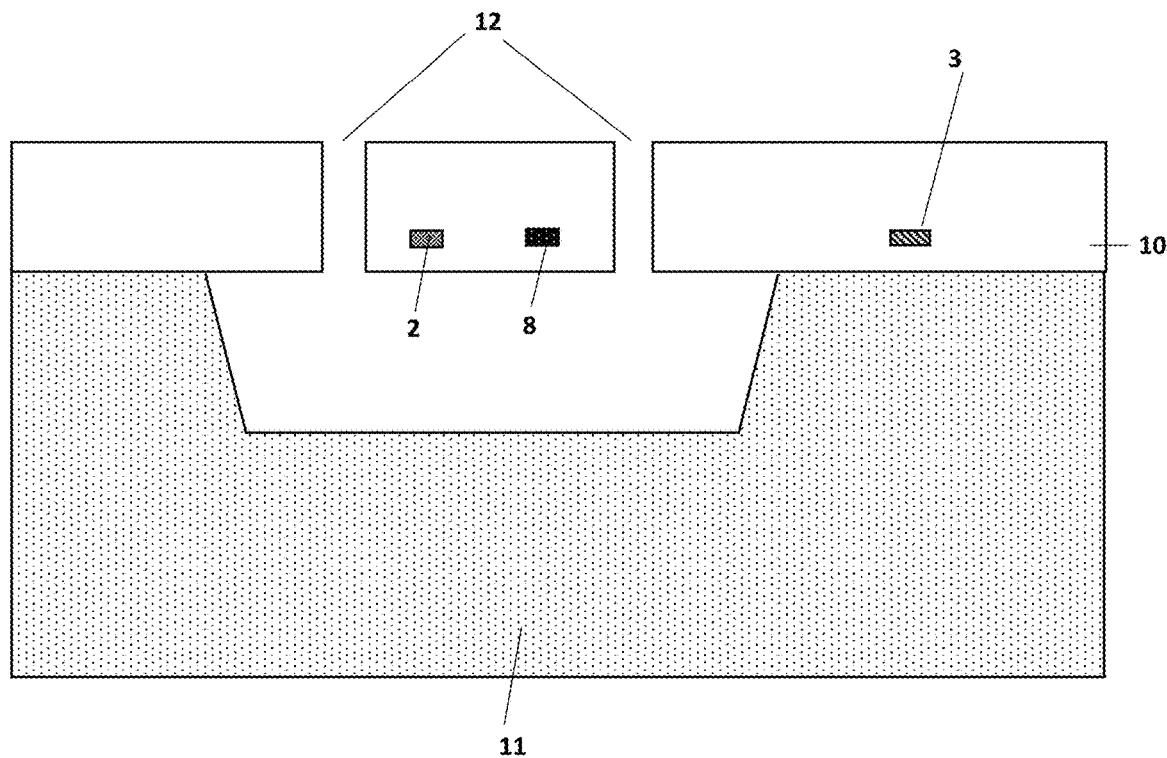

In FIG. 14a etching is performed such that it stops at the crystal plane of the semiconductor substrate 11, resulting in an etched region having a triangular profile. In FIG. 14b, the etching is isotropic, resulting in an etched region having a rounded profile. In FIG. 14c the etching is performed similar to FIG. 14a in that it stops at the crystal planes of the semiconductor substrate 11, but the stop point of the etching process is also controlled (for example by timing) so that it does etch completely, resulting in an etched region having a trapezoid profile.

Figure 15:
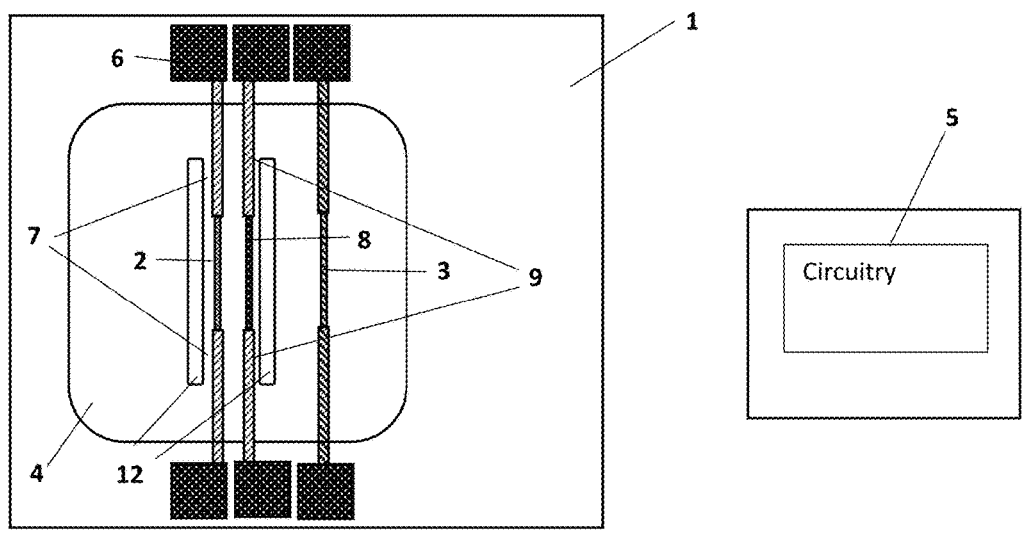
FIG. 15 shows the top view of a thermal conductivity fluid sensor where the second resistive temperature detector element (shown as a resistive wire) is also on the membrane.

FIG. 15 shows a top view of a thermal conductivity sensor design where both the first and second thermal detector elements 3, 8 are located on or within the same dielectric membrane 4. The heater element 2 and the second temperature detector 8 element are both located between two slotted recessed regions 12. The first temperature detector element 3 is thermally isolated from the first temperature detector element 8 and the heating element 2 by one of the slotted recessed regions 12. In this configuration, the heater element 2 and the second thermal detector element 8 are at substantially the same temperature during operation of the sensor, while the first thermal detector element 3 is at a different temperature, and is closer to the ambient temperature.

Figure 16A:
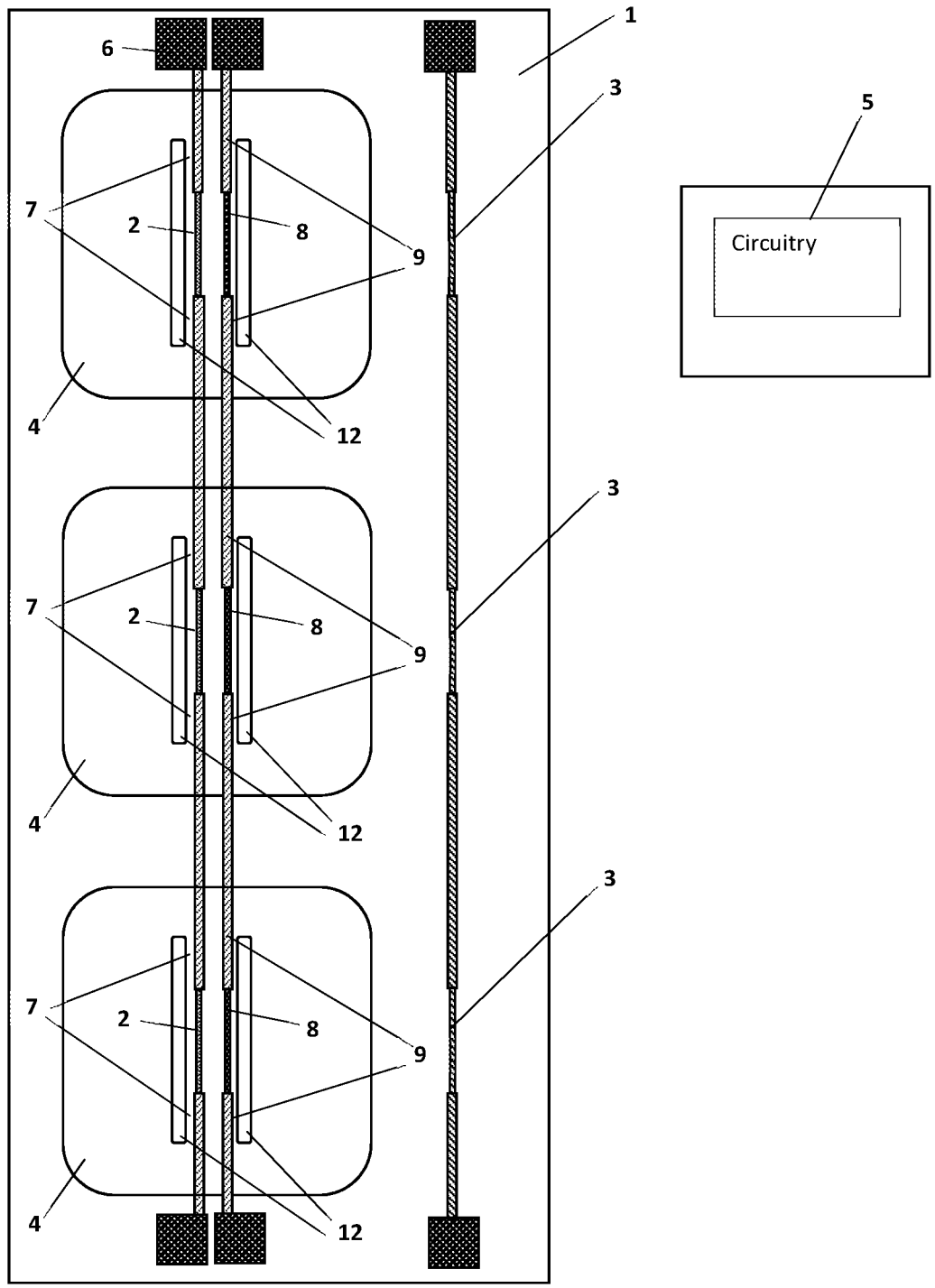
FIGS. 16(a) and 16(b) shows two alternative thermal conductivity fluid sensors comprising of an array of membranes and resistive temperature detectors.
Figure 16B:
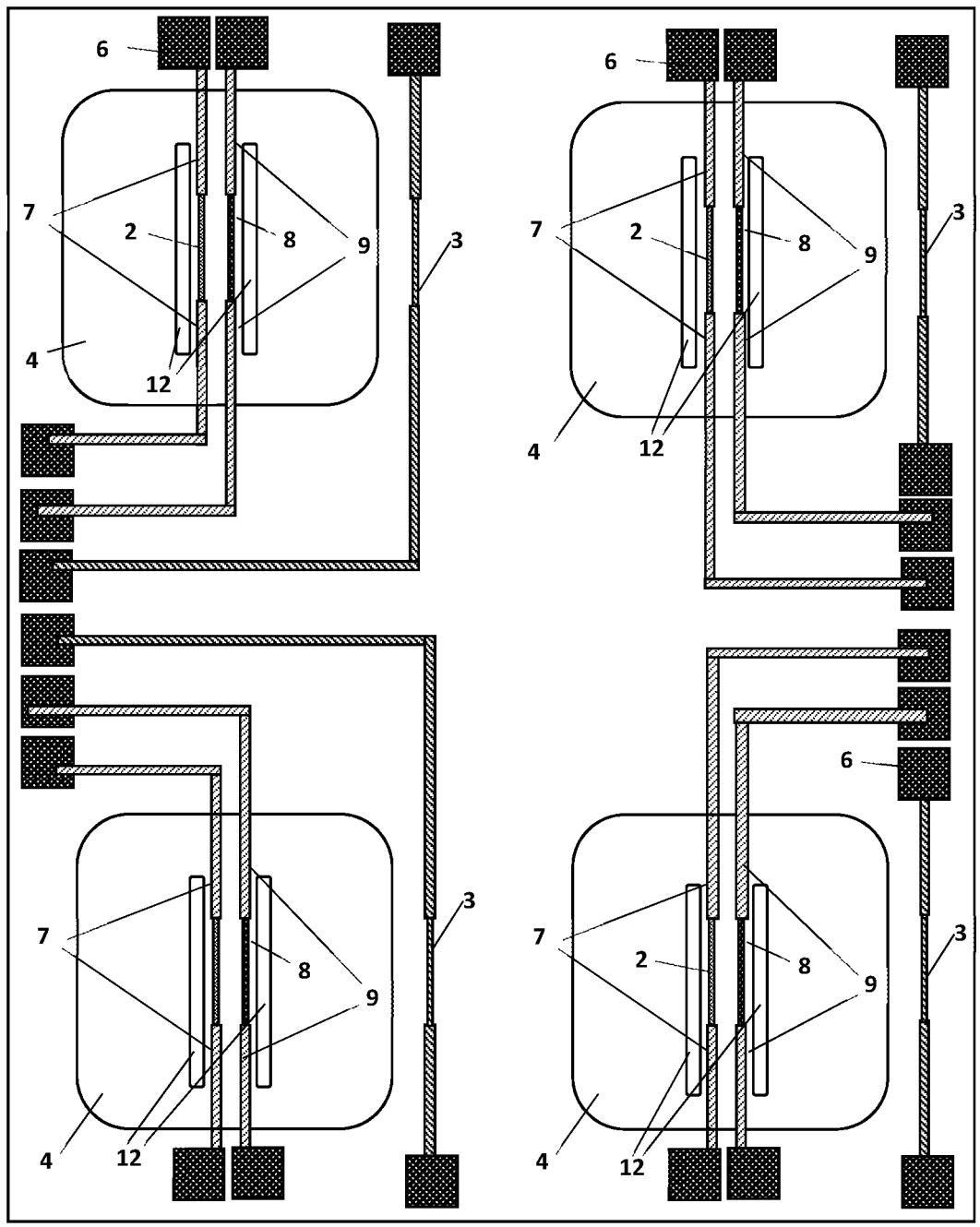

FIGS. 16a and 16b shows top views of two thermal conductivity fluid sensors each comprising an array of membranes.

In FIG. 16a there are three dielectric membranes 4, and the heater 2 and thermal detector elements 3, 8 from each membrane are connected in series. Each of the heating elements 2 are connected in series, each of the first temperature sensing elements 3 are connected in series, and each of the second temperature sensing elements 8 are connected in series. If this system is operated in a constant current mode for the heater 2 and the thermal detector elements 3, 8, then the differential voltage signal will be higher. In this example with three membranes and corresponding heating elements and temperature sensing elements, the differential voltage signal will be multiplied by three compared to sensors having a single dielectric membrane with a single heating element and first and second temperature detecting elements). This is given as an example, but greater or fewer number of membranes can also be used within the fluid sensor.

FIG. 16b shows an alternative thermal conductivity fluid sensor comprising 4 membranes, but the elements in each membrane are connected separately to bond pads. This allows much more flexibility in the design and use of the sensor. The four heaters 2 could be driven separately, for example at different temperatures, or with different drive modes. Alternatively, the heating elements 2 can be connected in series externally in a manner similar to FIG. 16a to increase the output signal.

Figure 17:
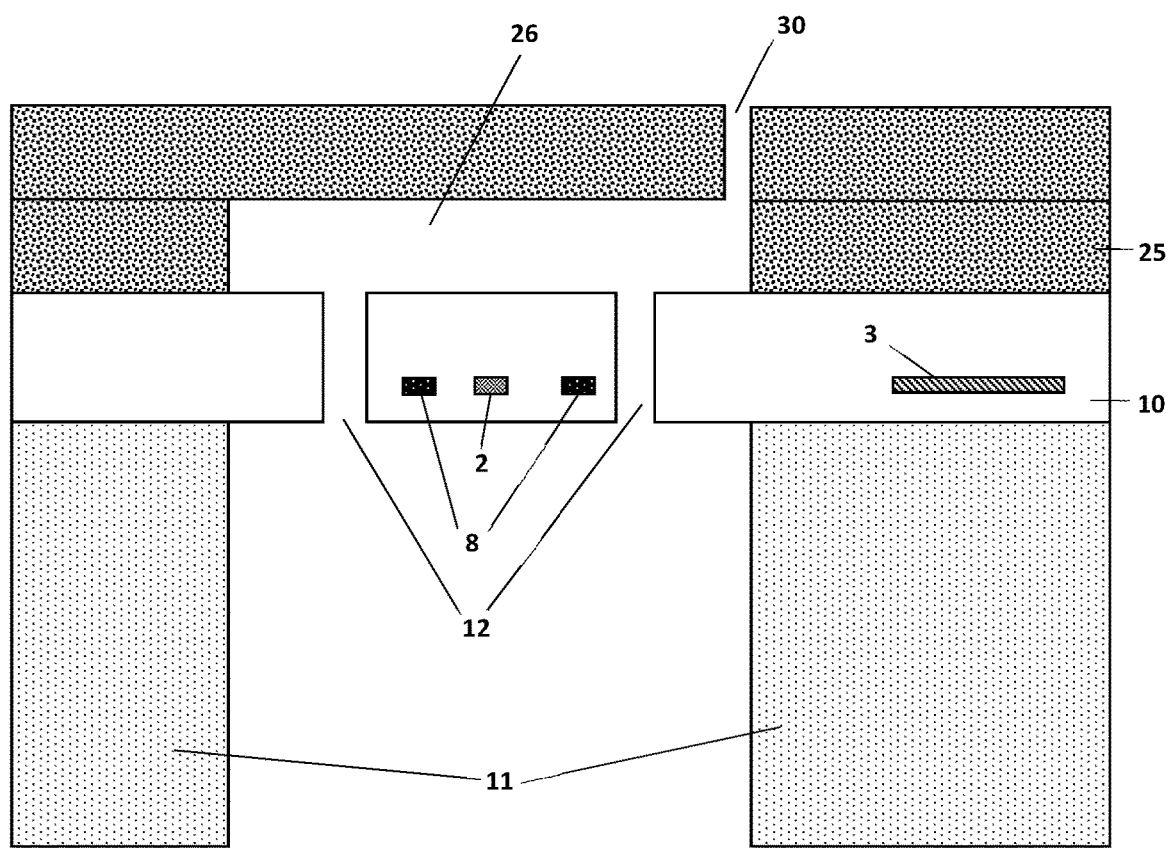
FIG. 17 shows a thermal conductivity fluid sensor packaged such that there is a very thin channel above the membrane.

FIG. 17 shows an cross section of a thermal conductivity fluid sensor where there is a covering 25 forming a very thin fluid channel 26 above the dielectric membrane of the dielectric layer 10. One or more holes 30 through the covering layer 25 allow fluid of various concentrations to diffuse or flow into the fluid channel region 26. The thin channel 26 increases the thermal losses from the heating element 2 to the fluid (from the membrane 4 to the covering 25) as the heat transferred through the fluid only needs to travel a smaller distance from the heating element 2 to the covering 25, the amount of heat loss through the fluid is increased. In embodiment without the covering 25, the heat needs to travel a greater distance to the closest solid surface (which may be the chip surface, as the heat transfer isn't required to be in a straight line). Therefore, the covering 25 increases the sensitivity of the device. The covering 25 can be a semiconductor bonded by wafer bonding. It can also be glass, or plastic.

Figure 18:
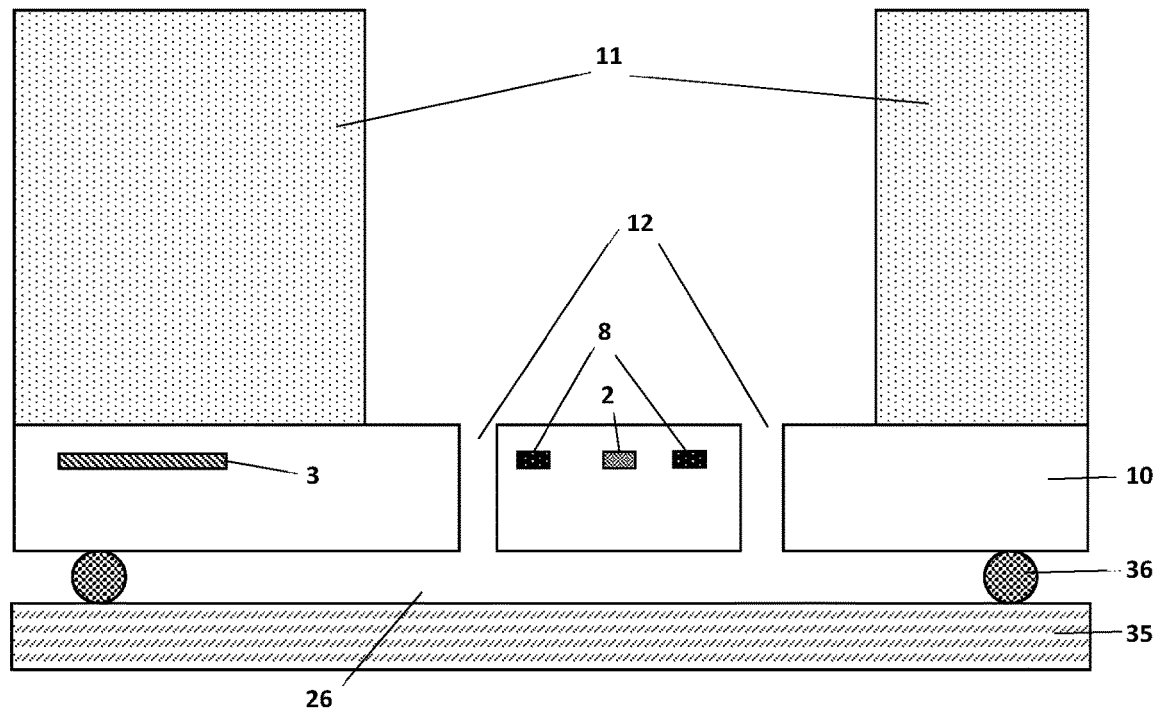
FIG. 18 shows a thermal conductivity fluid sensor packaged in a flip-chip configuration.

FIG. 18 shows a cross section of a thermal conductivity fluid sensor packaged in a flip chip method. Solder balls 36 form electrical connections to a Printed Circuit Board (PCB) 35. This also forms a thin channel 26 between the membrane of the dielectric layer 10 and the PCB 35, allowing for an increase in sensitivity of the device to fluid concentration similar to the device in FIG. 18.

Figure 19:
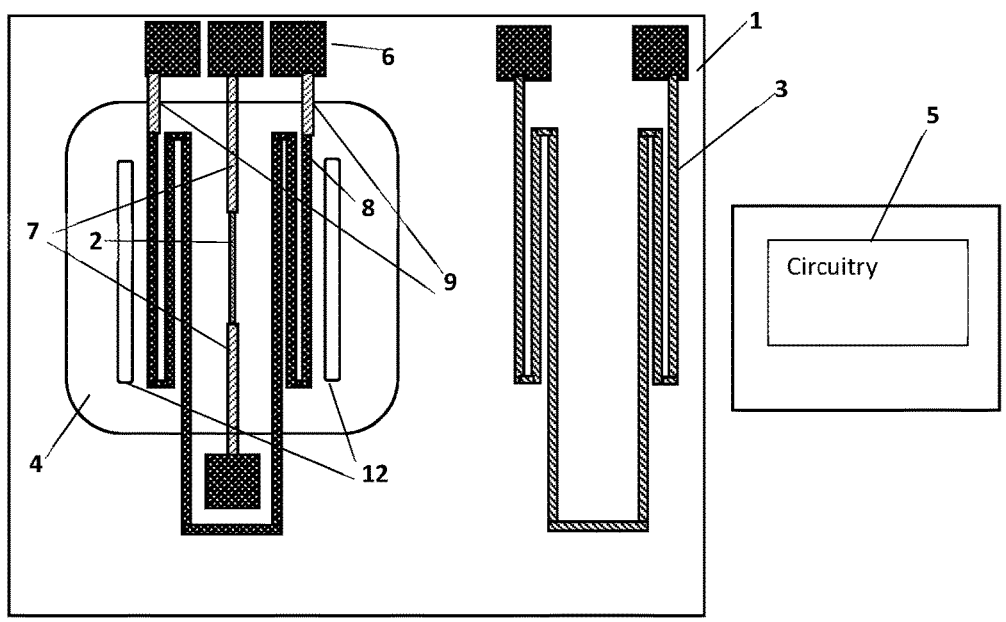
FIG. 19 shows the top view of a thermal conductivity fluid sensor with identical meander shaped resistive temperature detectors on and off the membrane.

FIG. 19 shows a top view of a thermal conductivity fluid sensor with the resistive temperature sensors 3, 8 having a meander shape. In particular, the second resistive temperature sensor 8 is configured such that the wire element of the second resistive temperature sensor 8 loops around one of the bond pads of the heater 2 and the second resistive temperature sensor 8 has two bond pads located on either side of the other bond pad of heater 2. This means that the second temperature sensing element 8 can be made in a single layer, and preferably within the same material layer as the heater 2. In this configuration, the first resistive temperature sensor 3 is the same shape as the second resistive temperature sensor 8, but is located outside the membrane region 4.

Figure 20:
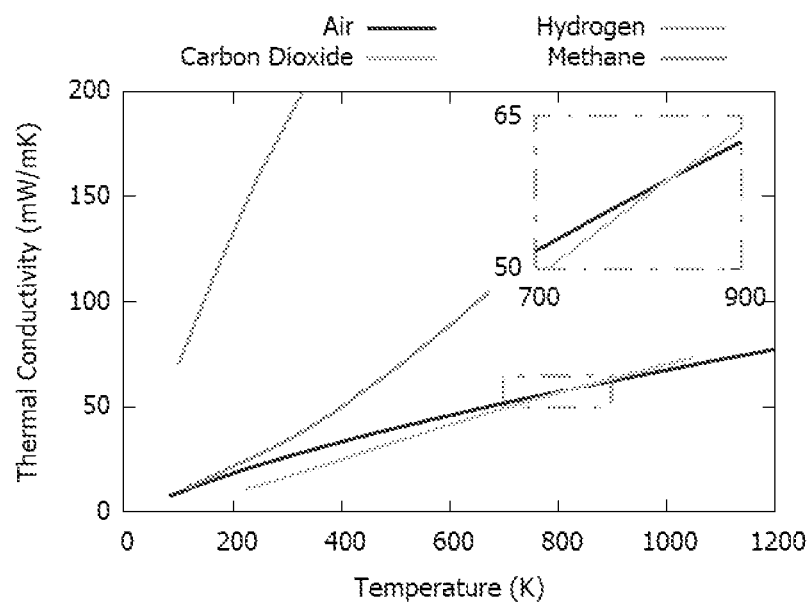
FIG. 20 shows a plot of gas thermal conductivity function with respect to the temperature for various gases.

FIG. 20 shows how the thermal conductivity measured by the fluid sensor varies with temperature for the gases of air, carbon dioxide, hydrogen and methane. This figure illustrates that the temperature dependence of gas thermal conductivity is different for different gas compositions. This means that heaters can be used at an optimum temperature for sensitivity of the device to different gases. In addition to this, the inset shows a detailed view of the temperature that air and carbon dioxide have the same value of thermal conductivity. This can be advantageous for the device selectivity, and multiple heater temperatures can be used to help identify, or ignore, certain gases (e.g. running the device at the temperature where carbon dioxide and air are identical eliminates any response to carbon dioxide in air).

Figure 21A:
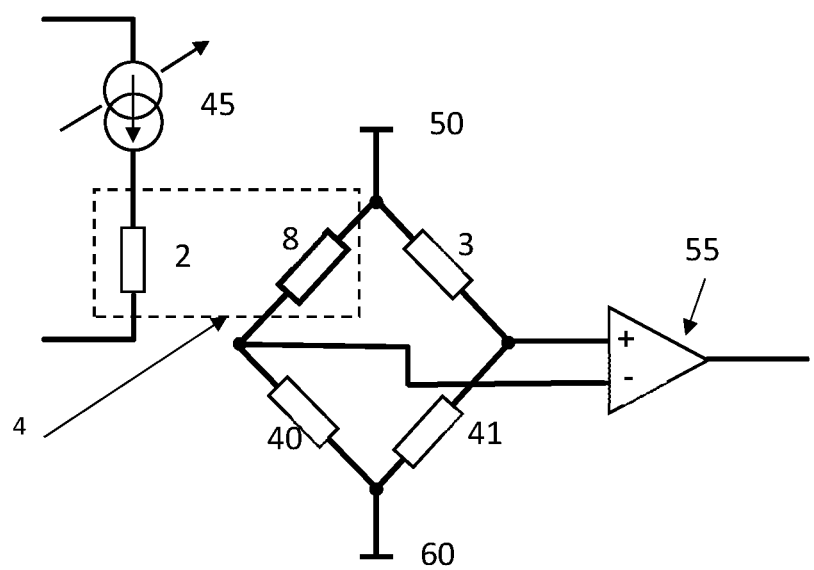
FIG. 21a shows a circuit diagram for measuring the thermal conductivity fluid sensor comprising a Wheatstone bridge.

FIG. 21a shows an example circuitry for driving a thermal conductivity fluid sensor and measuring the output from the sensor. This circuitry could be used in conjunction with any of the sensors described above having a heater 2, and first and second temperature sensing elements 3, 8. The heater 2 is driven by a current source. The first and second resistive temperatures sensors 3, 8 are located on sides of a wheatstone bridge along with two additional resistors 40 and 41. One side of the bridge (between the first and second resistive temperatures sensors 3, 8) is connected to a reference voltage 50, while the other side 60 is grounded. A differential amplifier 55 measures the differential voltage between the two legs of the wheatstone bridge.

The heater 2 may be drive with a constant current. When the concentration of the target gas changes, then the temperature of the heater 2, and hence the temperature and resistance of the second resistive temperature sensor 8 will change. This will change the differential voltage between the two arms of the wheatstone bridge and can be detected. The circuit may be calibrated in a standard environment (for example, with no target gas present) to know what the nominal or calibrated differential voltage is. Deviation from this calibrated differential voltage indicates presence of the target gas.

Preferably the resistors 40 and 41 are chosen such amplifier 55 outputs a zero voltage at a normal of calibrated condition (for example 0 ppm of the target gas in air, or in case the target gas is carbon dioxide then in 400 ppm of carbon dioxide in air). The resistors 40 and 41 may be trimmed during the calibration of the device. If resistors 40 & 41 are not chosen in such a way, then they may be calibrated to know what the differential voltage will be in the calibration conditions.

Another way to drive the fluid sensor is to control the current through the heater 2 such that the differential voltage across the Wheatstone bridge is always constant. In this case, the change in current required within the heater 2 could be measured to indicate the presence of a target gas.

Figure 21B:
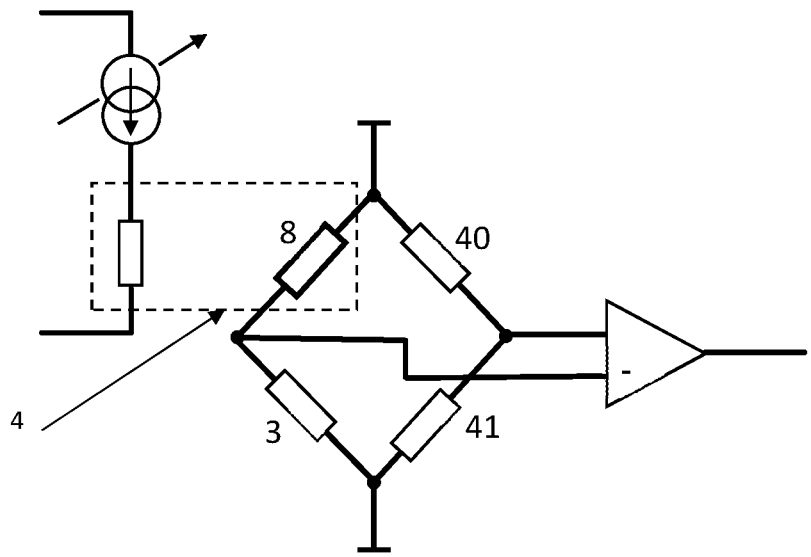
FIG. 21b shows an alternative circuit diagram for measuring the thermal conductivity fluid sensor comprising a Wheatstone bridge.

FIG. 21*b* shows another arrangement of the wheatstone bridge where the resistors 3 and 40 are swapped. Besides this many other arrangements of the bridge are possible.

Figure 21C:
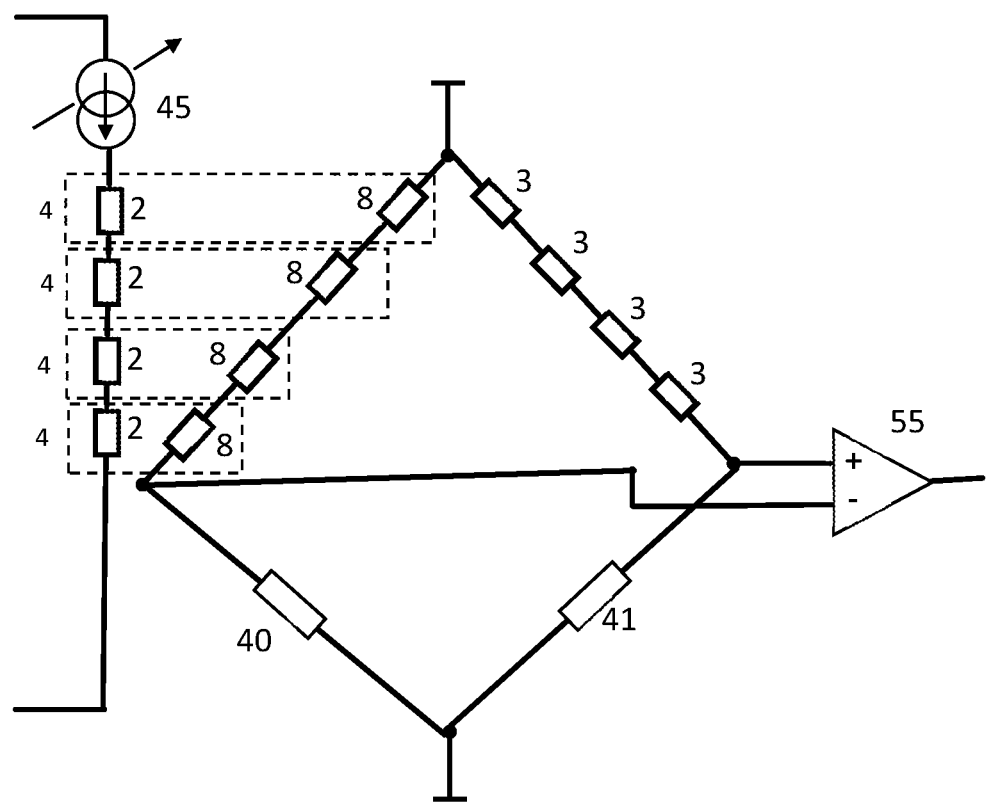
FIG. 21c shows a circuit diagram for measuring the thermal conductivity fluid sensor with a Wheatstone bridge, where the thermal conductivity sensor comprises an array of identical membranes.

FIG. 21*c* shows an example of circuitry for driving a thermal conductivity fluid sensor and measuring the output from the fluid sensor comprising an array of membranes and, heater and temperature sensor elements connected in series. This circuitry could be used in conjunction with either of the sensors shown in FIGS. 17*a* and 17*b*. The wheatstone bridge configuration of FIG. 22*b* can be used in a similar manner to that described in relation to FIG. 22*a*. The devices connected in this way can amplify the sensitivity due to increased voltage changes.

Figure 22:
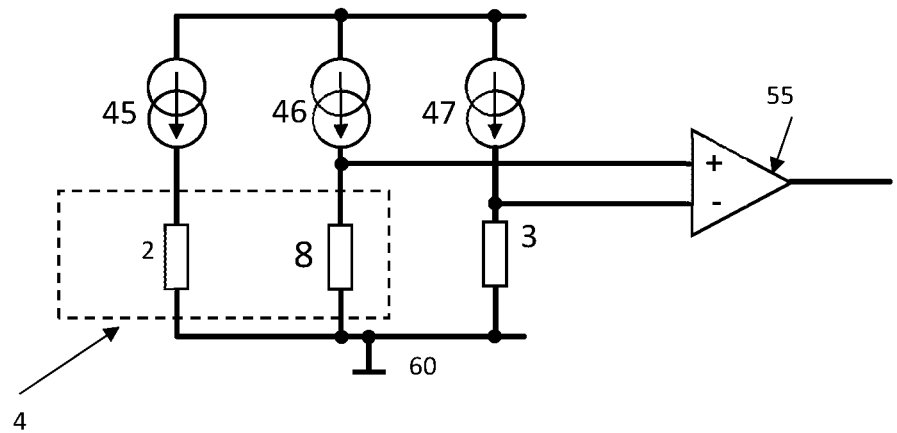
FIG. 22 shows a circuit diagram using constant current sources for both the resistive temperature detectors and the heating element.

FIG. 22 shows an example circuitry for driving a thermal conductivity fluid sensor and measuring the output from the sensor. The heater 2, and the first and second resistive temperature sensors 3, 8 are each driven by their own, separate current sources 45, 46, 47. Preferably, the fluid sensor is first calibrated in a standard, predetermined environment, and current sources 46 and 47 are adjusted such that the output from the differential amplifier 55 is zero. During operation, the current sources 46 and 47 are driven at the calibrated current levels, and the deviation of the output from zero of the differential amplifier 55 indicates the presence of the target gas.

Figure 23:
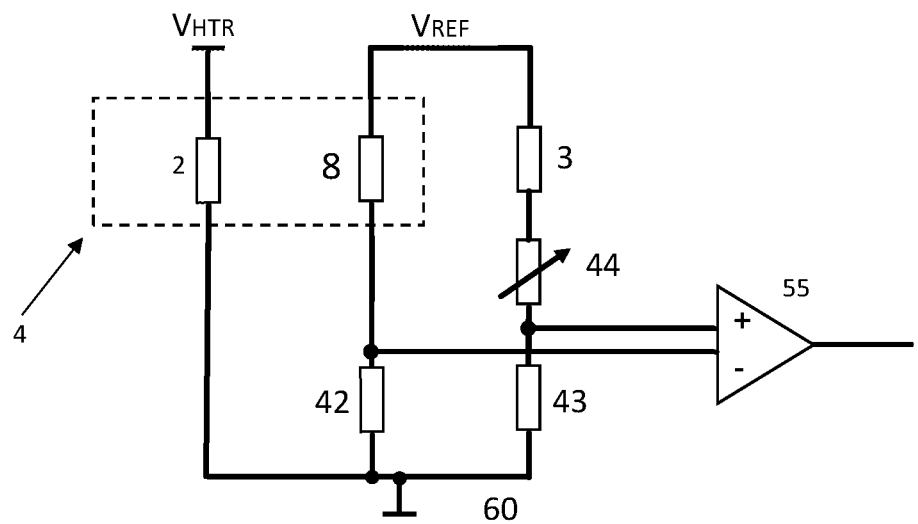
FIG. 23 shows a circuit diagram where the differential current between the two resistive temperature sensors is measured.

FIG. 23 shows alternative circuitry for driving a thermal conductivity fluid sensor and measuring the output from the sensor, having a Wheatstone bridge similar to FIG. 21. However, the heater 2 is driven by a voltage source $V_{HTR}$. Additionally the arm of the Wheatstone bridge that has the first resistive temperature sensor 3 also has a variable resistor 44 in series with the first resistive temperature sensor 3. The first and second resistive temperature sensors 3, 8 can have different resistances during heater operation, but during calibration the variable resistor 44 can be adjusted such that the output from the differential amplifier 55 is zero. The variable resistor 44 can be adjusted manually or electronically.

Figure 24:
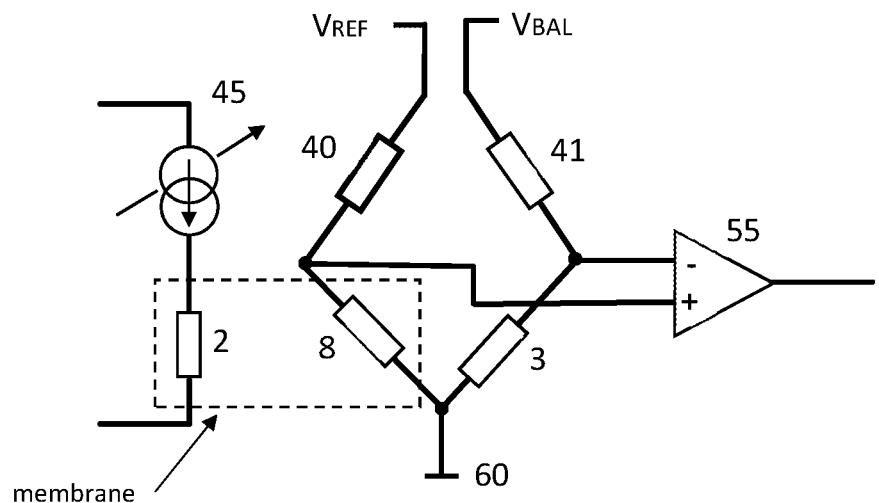
FIG. 24 shows a circuit diagram comprising a Wheatstone bridge where each arm of the bridge can have a different voltage applied to keep the bridge balanced.

FIG. 24 shows alternative circuitry for driving a thermal conductivity fluid sensor and measuring the output from the sensor, however each side of the bridge has a different supply voltage. One side is kept constant at $V_{REF}$, while the other is kept at an adjustable voltage $V_{BAL}$. During calibration, $V_{BAL}$ can be adjusted so that the differential amplifier 55 gives an output of zero volts. This $V_{BAL}$ value can then be stored in either in firmware or software of the sensor. This $V_{BAL}$ value is then applied whenever the device is operated, and deviation of the differential amplifier output from zero indicates the presence and concentration of the target gas. In an alternate configuration, $V_{BAL}$ can be controlled during operation to keep the output signal at zero, and changes in the required $V_{BAL}$ value can be measured to indicate the presence of a gas.

Figure 25:
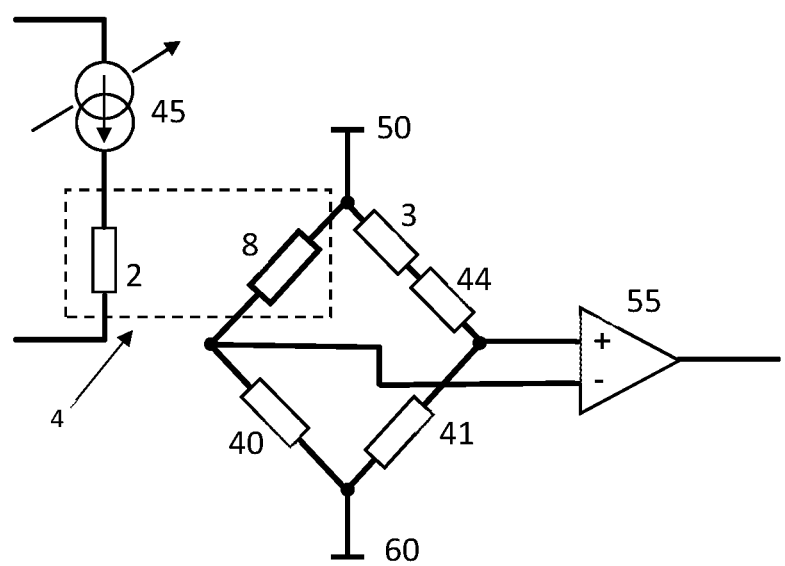
FIG. 25 shows a circuit diagram with a Wheatstone bridge and a balancing resistor in the branch with the reference resistive temperature detector.

FIG. 25 shows alternative circuitry for driving a thermal conductivity fluid sensor and measuring the output from the sensor comprising a wheatstone bridge with a variable resistor 44 similar to FIG. 23, but the heater is driven using a current source.

Figure 26:
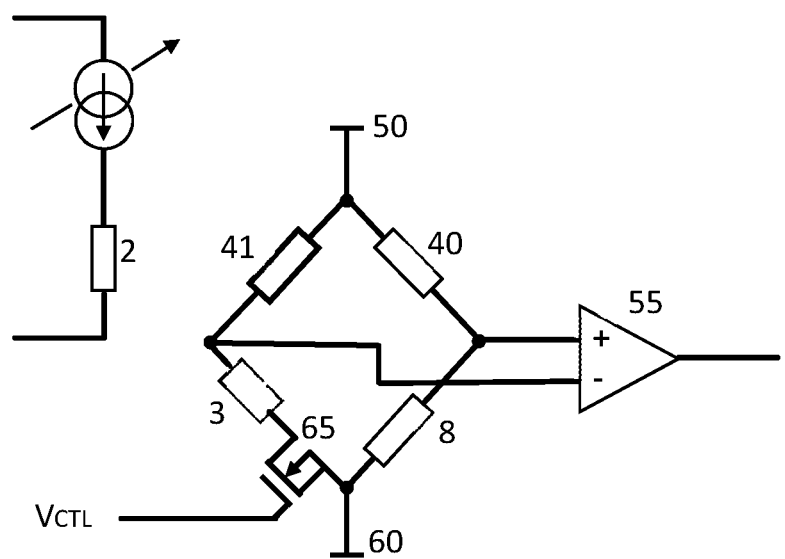
FIG. 26 shows a circuit diagram with a Wheatstone bridge, with the reference resistive temperature detector in series with a transistor.

FIG. 26 shows alternative circuitry for driving a thermal conductivity fluid sensor and measuring the output from the sensor. The first and second resistive temperature sensors 3, 8 are both in the bottom side of the Wheatstone bridge. Furthermore, the branch comprising the first resistive temperature sensing element 3 also has a Field Effect Transistor (FET) 65 in series with the first resistive temperature sensing element 3. The FET 65 is similar to the variable resistor of FIG. 25, however this can be controlled electronically allowing calibration without manual intervention.

Figure 27:
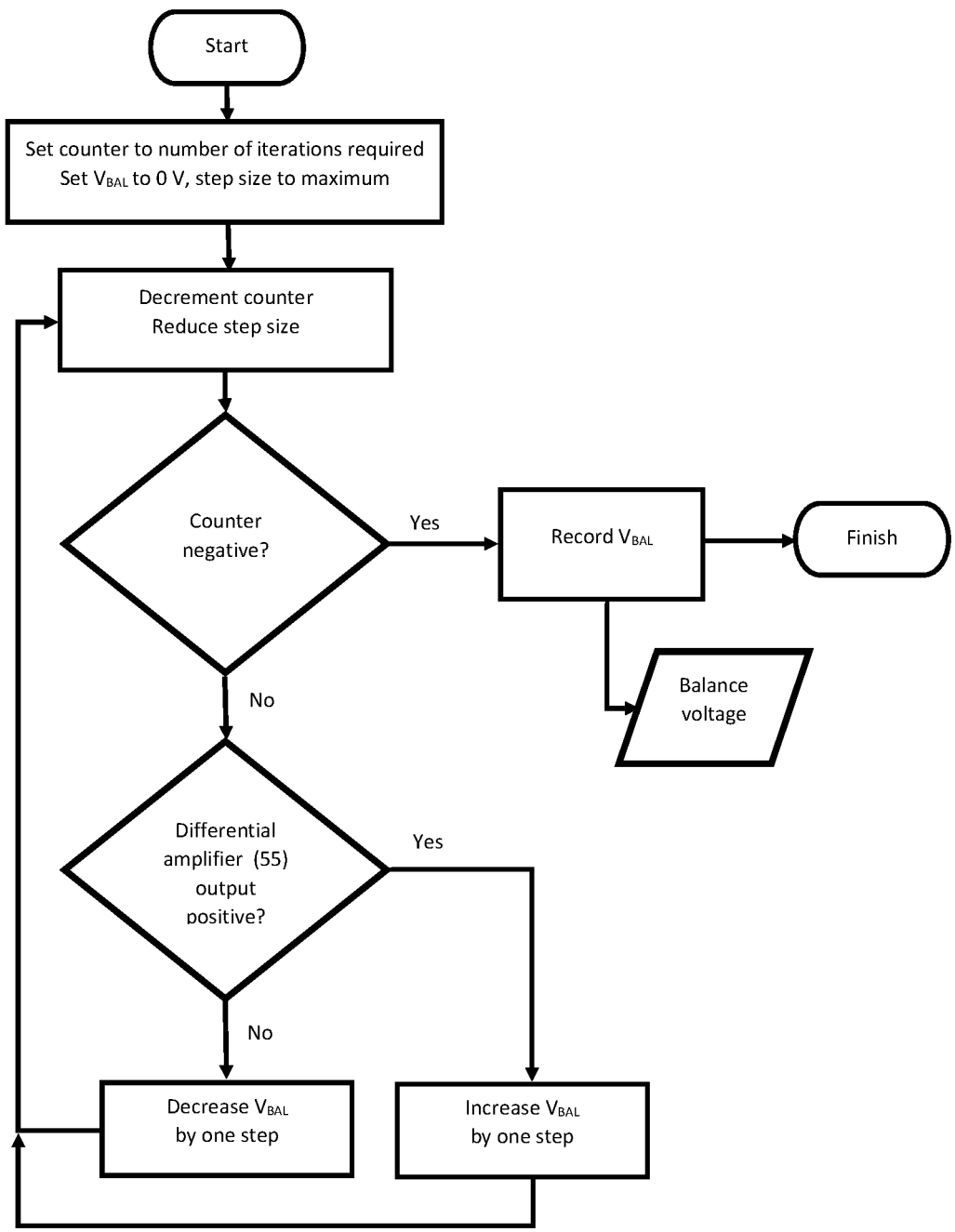
FIG. 27 shows a flow chart giving a method that can be used to electronically balance the Wheatstone bridge.

FIG. 27 shows steps in of a method of balancing the Wheatstone bridge shown in FIG. 24. This method uses a fixed number of iterations. A counter is set to the maximum number of iterations. At each iteration, the counter is reduced by 1. If the value of the counter is negative then the current $V_{BAL}$ value is set as the balance voltage. Otherwise, the output from the differential amplifier is checked. If the output is positive, then the $V_{BAL}$ value is increased, otherwise it is decreased.

This method can be used in two ways. It can be used in calibration of the fluid sensor to determine the required balance voltage at a standard environment. Alternatively, it can be used during operation of the fluid sensor to keep the Wheatstone bridge balanced, and the $V_{BAL}$ value can be measured to determine presence and concentration of gas.

Other similar method or algorithms can also be used; for example, counting up to a maximum number of iterations, or performing iterations until the absolute output from the differential amplifier is within the required range, or a mixture of the method described above.

Figure 28:
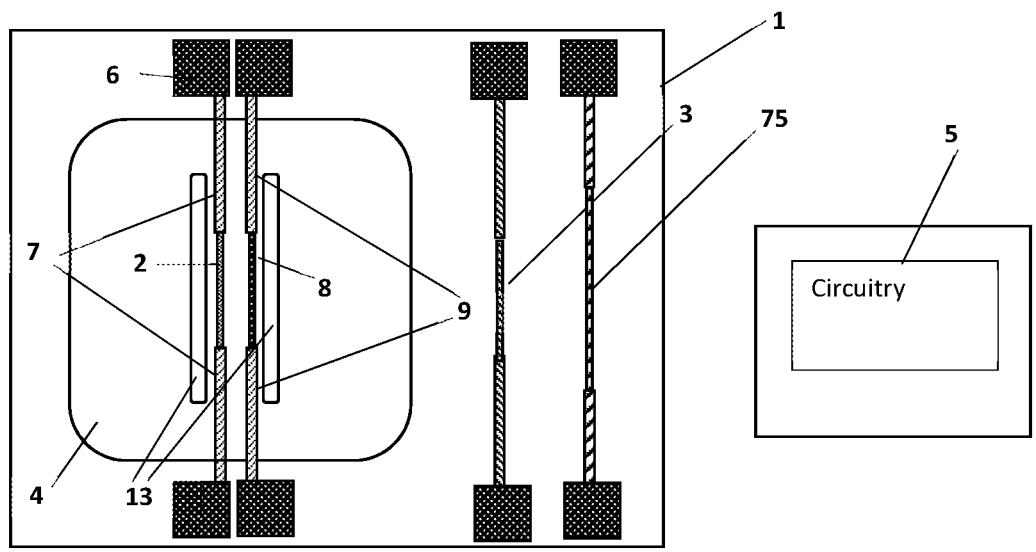
FIG. 28 shows a top view of the thermal conductivity sensor, with an additional on-chip temperature sensor to determine the ambient temperature, or the die temperature.

FIG. 28 shows the top view of a thermal conductivity fluid sensor where there is an additional temperature sensing element 75 on the chip, and outside the dielectric membrane 4. This additional temperature sensing element 75 can be used to compensate for effects of ambient temperature changes. Most effects of ambient temperature changes will be cancelled out due to the differential measurement method of the fluid sensor. However, compensating for ambient temperature changes using a temperature sensing element 75 will further improve accuracy. The additional temperature sensing element 75 shown in the figure is a resistive temperature sensor. However, it can also be a diode, transistor or a standard temperature measurement circuit such as an iptat or a vptat circuit.

Figure 29A:
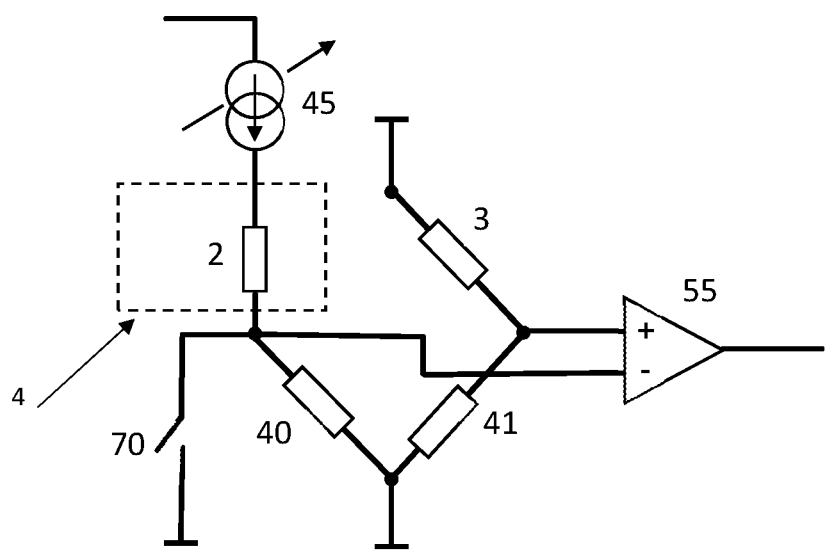
FIG. 29(a) shows a circuit diagram where a single resistor is used both as the heater and the first resistive temperature sensor element of the fluid sensor.

FIG. 29*a* shows alternative circuitry for driving a thermal conductivity fluid sensor and measuring the output from the sensor where a single resistor 2 is used as the heater and the second resistive temperature sensing element, similar to the sensor shown in FIG. 1. In this sensor there is a bridge circuit having two sides. One side has the first resistive temperature sensing element 3, and an additional resistor 41. The other side comprises the heating resistor 2 and a further additional resistor 40, with resistor 40 ideally identical to resistor 41. When using the resistor 2 to measure sensing, the current from the current source 45 flows through resistors 2 and 40. The signal at the output of the differential amplifier 55 will be dependent on the temperature of resistor 2. When using resistor 2 for heating, a switch 70 is closed, allowing a larger current to flow.

Figure 29B:
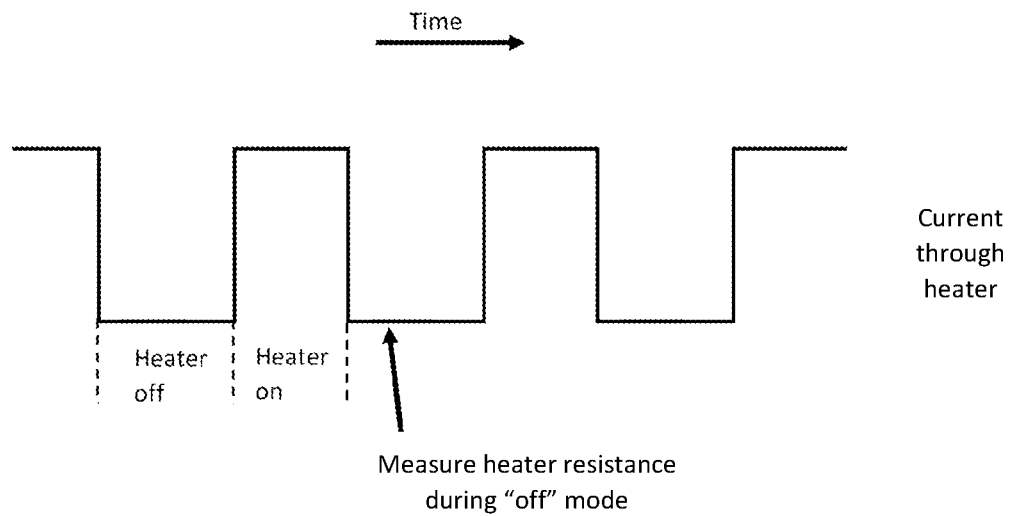
FIG. 29(b) shows the current through the heater of the sensor of FIG. 30(a)

FIG. 29*b* shows a PWM (Pulse Width Modulation) waveform which shows with time the current and/or voltage in the heater of FIG. 29*a*. The pulses have a high frequency such that there is little change in heater temperature during the "off" mode of the pulsed heater. During the "off" mode the resistance of the heater can be measured to determine the heater temperature, and a differential signal between the temperature of the heating element and the first temperature sensing element can be used to determined thermal conductivity of the fluid in the sensor. This method can be used in cases where the heater is also used as the second resistive temperature detector element as shown in FIG. 29a, by opening and closing the switch 70.

Figure 30:
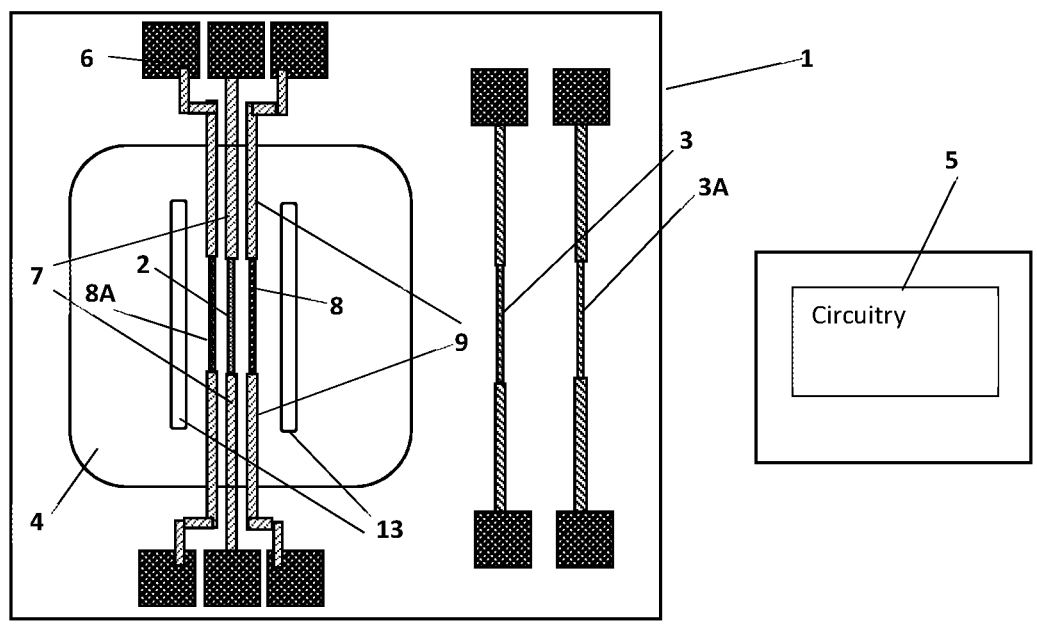
FIG. 30 shows a top view of the thermal conductivity fluid sensor where there are two resistive temperature detectors within the membrane region and two resistive temperature detectors outside the membrane region.

FIG. 30 shows a top view of a thermal conductivity fluid sensor where in addition to the first and second temperature detector elements 3, 8 there are two additional temperature detector elements 3A, 8A. Temperature sensing elements 8 and 8A are both on or within the dielectric membrane 4 and in close proximity to the heater 2, whereas temperature sensing elements 3 and 3A are outside the membrane region 4.

Figure 31:
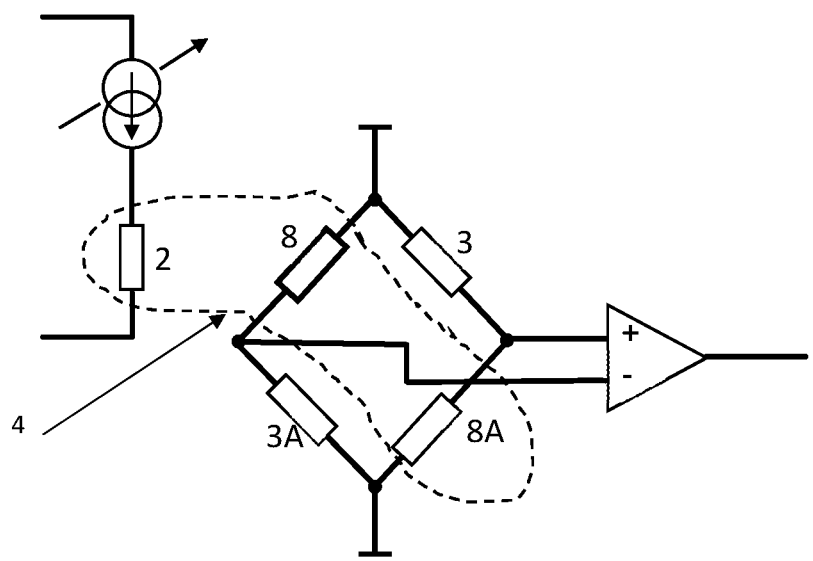
FIG. 31 shows a circuit diagram of the thermal conductivity fluid sensor for the configuration where there are two resistive temperature detectors within the membrane region, and two outside the membrane region.

FIG. 31 shows circuitry for driving the thermal conductivity fluid sensor and measuring the output from the thermal conductivity fluid sensor shown in FIG. 31. The second temperature detector elements that are on the membrane 8, 8A are placed on opposite sides of the Wheatstone bridge. Similarly, both the first temperature detector elements outside the membrane region 3, 3A are also placed on opposite sides to each other. This configuration doubles the sensitivity of the thermal conductivity sensor.

Figure 32:
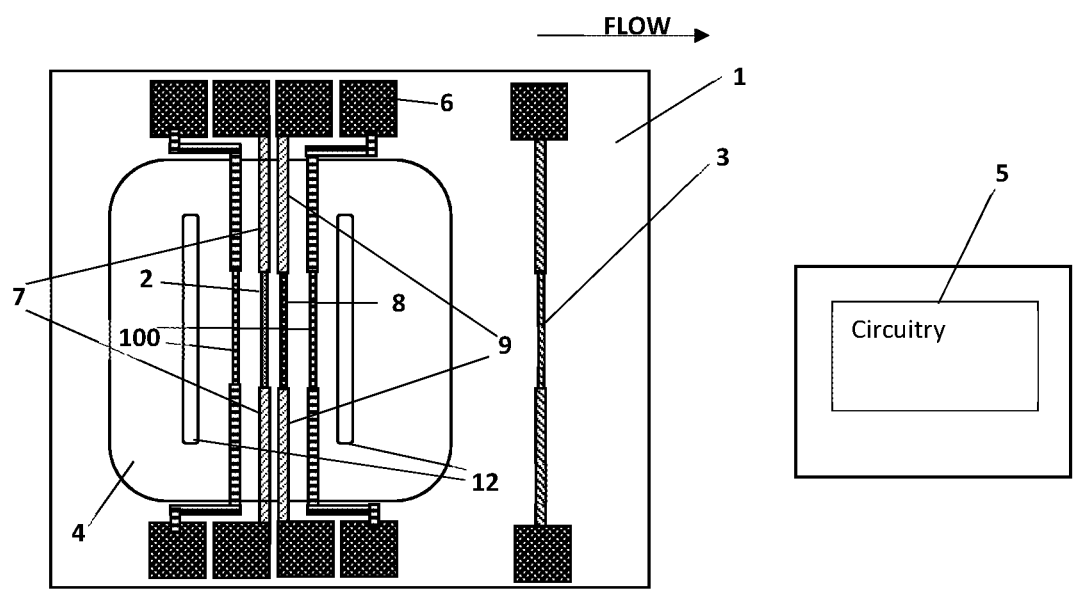
FIG. 32 shows a top view of a thermal conductivity fluid sensor having a further pair of sensing elements configured to operate as a flow sensor.

FIG. 32 shows the top view of a thermal conductivity fluid sensor comprising two additional resistive elements 100 either side of the heater 2 and the second temperature detector element 8. This allows the device to be used as not only a thermal conductivity sensor, but also a flow sensor. One resistive element of the pair of resistive elements 100 is located upstream of the heating element 2 and another resistive element of the pair of resistive elements 100 is located downstream of the heating element 2. The heating element 2 extends in a direction substantially perpendicular to the direction of flow through the sensor. When the fluid passes over the top of the membrane 4, the heater 2 cools down due to heat convention losses. In the presence of the flow, the downstream sensing element sees a higher temperature than the upstream sensing element. The temperature difference between the pair of resistive elements 100 increases with the flow rate (or flow velocity). In the presence of a fluid flow, there will be a difference in resistance between the two additional resistive elements 100 depending on the speed and direction of the fluid flow. Whilst shown as resistive elements, the two additional elements 100 for flow sensing can be based on other temperature detection principles such as diode based temperature detectors, or a thermopile temperature detector.

Figure 33:
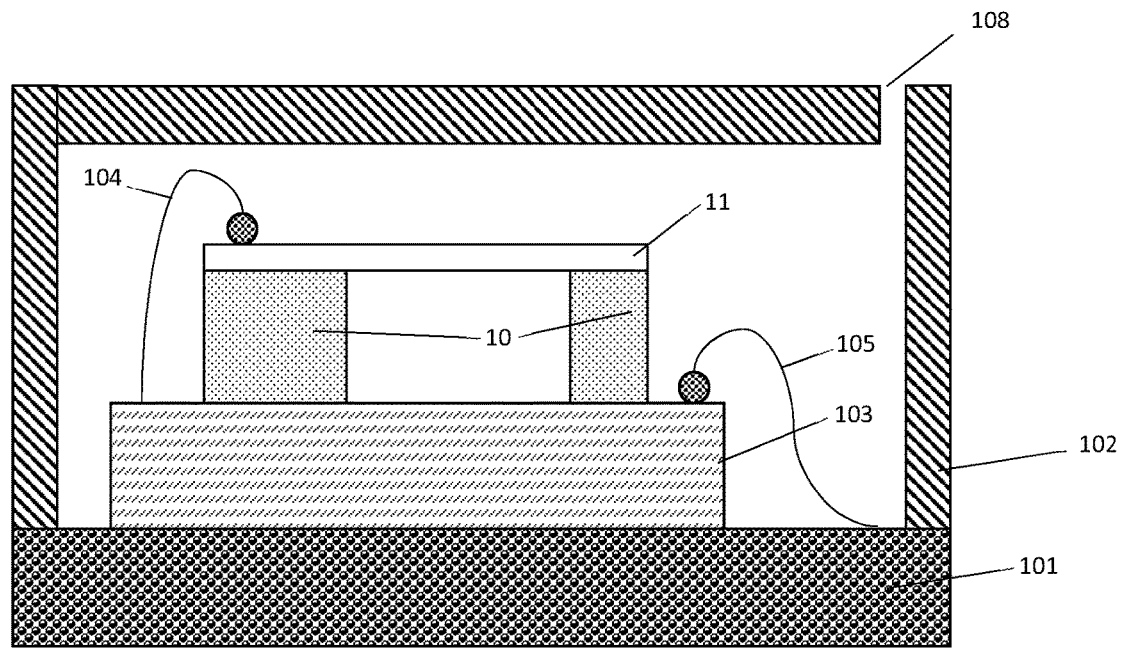
FIG. 33 shows the cross-section of a fluid sensor assembly having a thermal conductivity fluid sensor contained in a package.

FIG. 33 shows a cross-section of a thermal conductivity fluid sensor assembly. It comprises a package base 101 and a package lid 102. Within the package is an ASIC (Application Specific Integrated Circuit) chip 103 that is used to control and measure the thermal conductivity sensor chip. Above this ASIC chip 103 is the thermal conductivity sensor chip comprising a substrate 10 and dielectric region or layer 11. The sensor chip may include any fluid sensor as described above. Wire bonds 104 electrically connect the thermal conductivity sensor fluid chip to the ASIC chip 103, and wire bonds 105 electrically connect the ASIC 103 to the package base 101. A hole 108 within the package lid 102 allows the ambient air or gas to diffuse into the package and around the thermal conductivity sensor. More than one hole may be present within the package lid, and the size and shape of the hole 108 can be varied, and filters may be placed around or within the hole 108 or holes to protect against particles or liquids.

Figure 34:
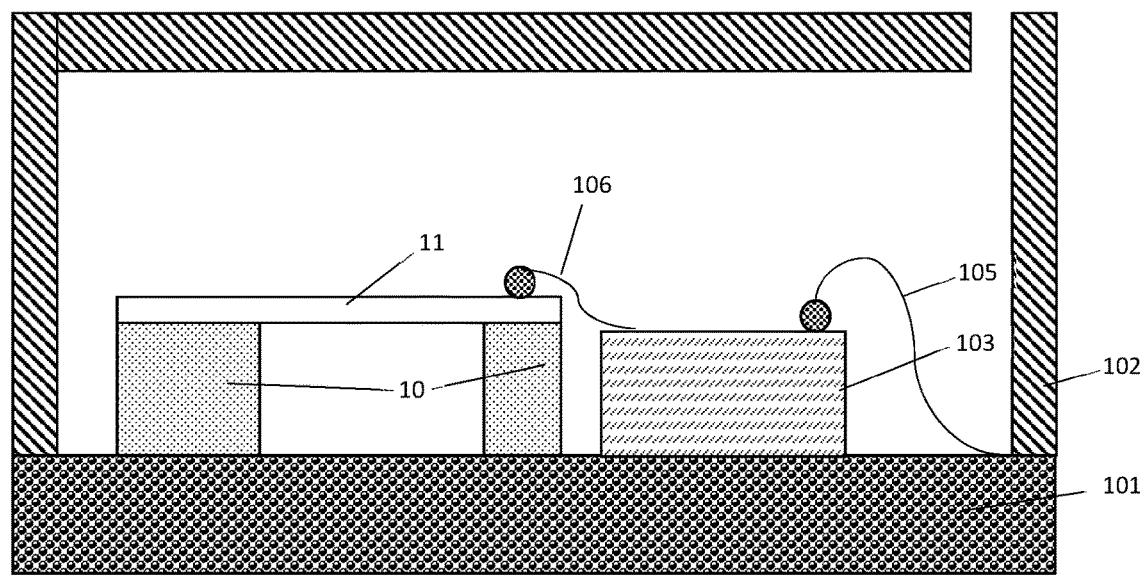
FIG. 34 shows the cross-section of an alternative fluid sensor assembly having a thermal conductivity fluid sensor contained in a package.

FIG. 34 shows a cross-section of an alternative thermal conductivity fluid sensor assembly. The ASIC chip 103 and the fluid sensor chip are not stacked on top of each other, but are located side by side within the package. Wire bonds 106 connect the sensor chip to the ASIC chip 103.

Figure 35:
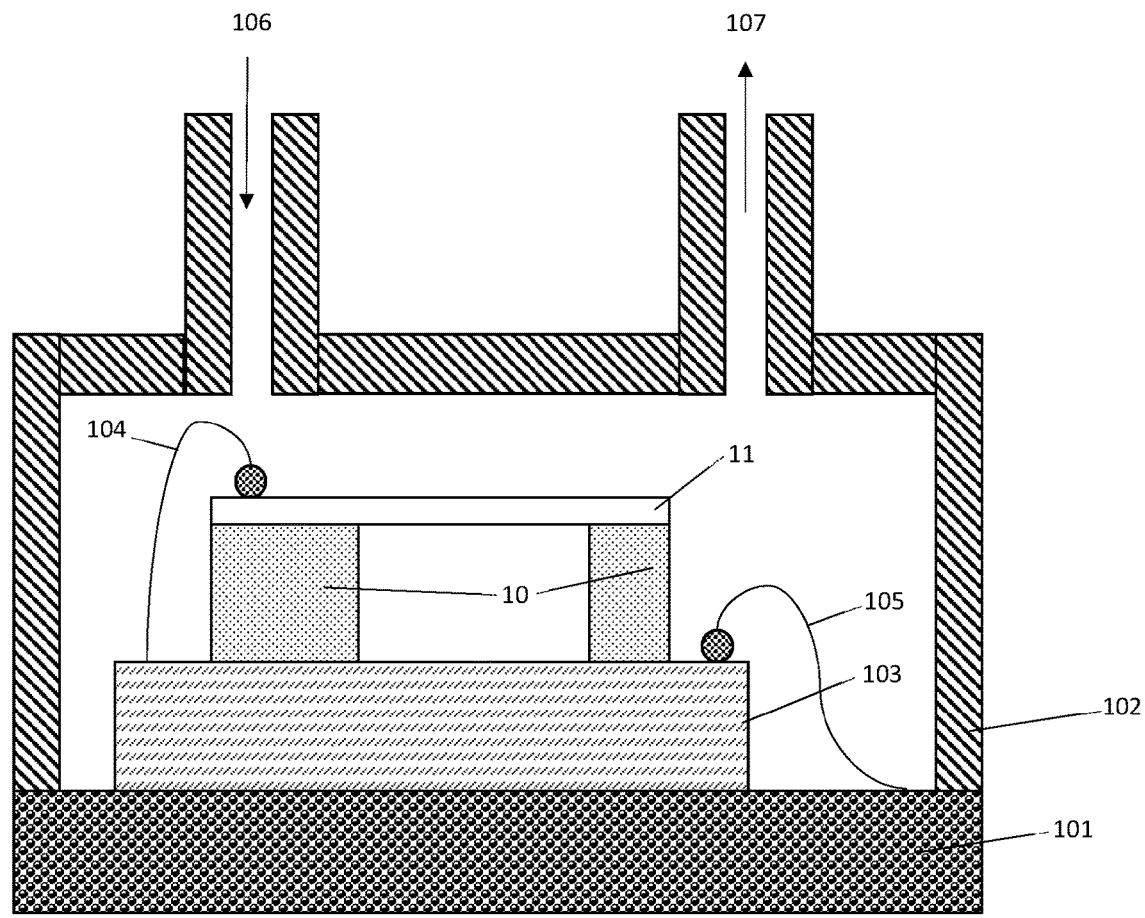
FIG. 35 shows the cross-section of an alternative fluid sensor assembly having a thermal conductivity fluid sensor contained in a package.

FIG. 35 shows a cross-section of an alternative thermal conductivity fluid sensor assembly. Compared to the sensor assemblies shown in FIGS. 33 and 34, the lid 102 has two ports, one as an input port 106 and one as an output port 107.

Figure 36:
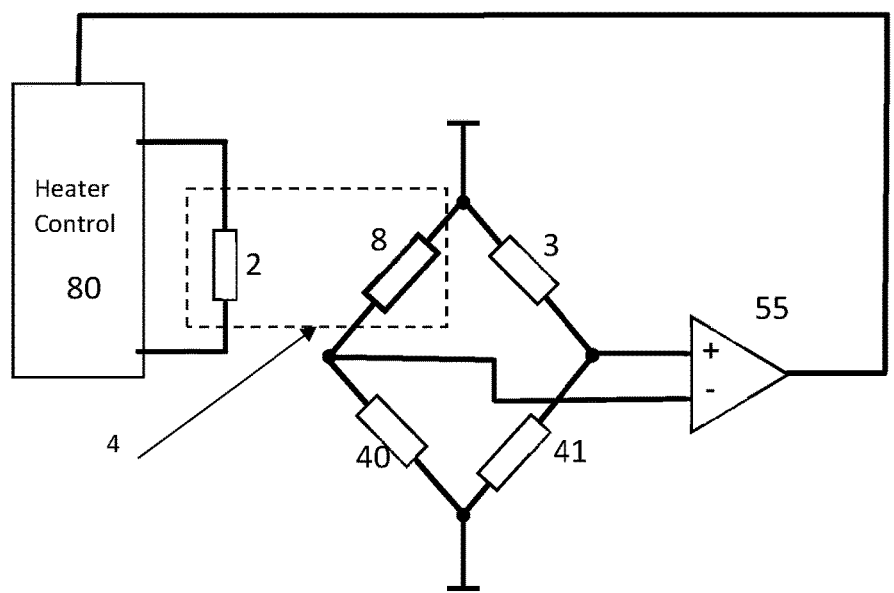
FIG. 36 shows a circuit diagram of a thermal conductivity fluid sensor where the heater is controlled via a feedback loop from the differential amplifier.

FIG. 36 shows alternative circuitry for driving a thermal conductivity fluid sensor and measuring the output from the sensor. There is a circuit block 80 to control the heater 2. The output from the instrumentation amplifier 55 is part of a feedback loop into the heater control 80. The heater 2 can then be controlled such that it keeps the output of the instrument amplifier 55 at zero voltage. The bias or control signal required to the heater 2 is then used to determine presence and concentration of gas within the fluid sensor.

The skilled person will understand that in the preceding description and appended claims, positional terms such as 'above', 'overlap', 'under', 'lateral', etc. are made with reference to conceptual illustrations of an device, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

| Reference Numerals | |
|---|---|
| 1 | Semiconductor chip |
| 2 | Resistive heating element |
| 2A | Additional heating element |
| 3 | First temperature sensing element |
| 3A | Additional first temperature sensing element |
| 4 | Dielectric membrane |
| 4a | Second dielectric membrane |
| 5 | Circuitry |
| 6 | Bond pads |
| 7 | Track |
| 8 | Second temperature sensing element |
| 8A | Additional second temperature sensing element |
| 9 | Tracks |
| 10 | Dielectric layer |
| 11 | Semiconductor substrate |
| 12 | Elongate slot |
| 13 | Hole |
| 20 | Connecting element |
| 25 | Covering layer |
| 26 | Fluid channel above membrane |
| 30 | Hole through covering layer |
| 35 | Printed Circuit Board |
| 36 | Solder balls |
| 40, 41 | Additional resistor |
| 42, 43 | Additional resistor |
| 44 | Variable resistor |
| 45, 46, 47 | Current source |
| 50 | Reference voltage |
| 55 | Differential amplifier |

-continued

| Reference Numerals | | |
|---|---|---|
| 60 | | Ground |
| 65 | | Field Effect Transistor |
| 70 | | Switch |
| 75 | | Ambient temperature sensing element |
| 80 | | Heater control |
| 100 | | Pair of temperature sensing elements |
| 101 | | Package base |
| 102 | | Package lid |
| 103 | | ASIC |
| 104, 105 | | Wire bonds |
| 106 | | Inlet |
| 107 | | Outlet |
| 108 | | Hole through package lid |
| 110 | | Lid |
| 201 | | Dummy elements |

The invention claimed is:

1. A fluid sensor for sensing a concentration or composition of a fluid, the sensor comprising:
a semiconductor substrate comprising a first etched portion;
a dielectric region located on the semiconductor substrate, wherein the dielectric region comprises a first dielectric membrane located over the first etched portion of the semiconductor substrate;
a heating element located on or within the first dielectric membrane; and
a first temperature sensing element spatially separated from the heating element, wherein the first temperature sensing element is located outside of the first dielectric membrane and positioned away from the first etched portion
wherein the heating element is further configured to operate as a second temperature sensing element, and wherein the separation between the second temperature sensing element and the first temperature sensing element introduces a temperature difference between the heating element and the first temperature sensing element, such that a differential signal between the first temperature sensing element and the second temperature sensing element is indicative of the concentration or composition of the fluid based on a thermal conductivity of the fluid.

2. A fluid sensor for sensing a concentration or composition of a fluid, the sensor comprising:
a semiconductor substrate comprising a first etched portion;
a dielectric region located on the semiconductor substrate, wherein the dielectric region comprises a first dielectric membrane located over the first etched portion of the semiconductor substrate;
a heating element located on or within the first dielectric membrane;
a first temperature sensing element spatially separated from the heating element, wherein the first temperature sensing element is located outside of the first dielectric membrane and positioned away from the first etched portion; and
a second temperature sensing element located on or within the first dielectric membrane
wherein a separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

3. The fluid sensor according to claim 2, wherein the second temperature sensing element is located in a same layer of the dielectric region as the heating element and wherein the second temperature sensing element laterally surrounds the heating element, or
wherein the second temperature sensing element is located below or above the heating element.

4. The fluid sensor according to claim 2, wherein the first temperature sensing element is configured to have a higher resistance at room temperature than a resistance of the second temperature sensing element at room temperature, and wherein the first temperature sensing element and the second temperature sensing element are configured to have substantially the same resistance at an operating temperature of the sensor without a fluid present.

5. The fluid sensor according to claim 2, wherein the heating element is a resistive heating element; and/or wherein at least one of the first temperature sensing element and the second temperature sensing element are resistive temperature sensing elements.

6. The fluid sensor according to claim 2, further comprising circuitry configured to determine the concentration or composition of the fluid based on the differential signal; and optionally wherein the circuitry may be located on a same chip as the fluid sensor.

7. The fluid sensor according to claim 6, wherein the circuitry comprises one or more of:
a constant current or constant resistor drive circuit,
a constant current source,
a Wheatstone bridge,
an amplifier, an Analog to Digital converter,
a Digital to Analog Converter, or
a microcontroller.

8. The fluid sensor of claim 6, wherein the first temperature sensing element and the second temperature sensing are located on two sides of a bridge circuit, and wherein the sensor is configured such that an output of the bridge circuit is a function of the thermal conductivity of the fluid around the sensor.

9. The fluid sensor according to claim 2, wherein the semiconductor substrate comprises an additional etched portion, and wherein the dielectric region comprises an additional dielectric membrane located over the additional etched portion of the semiconductor substrate, and
wherein the sensor further comprises:
an additional heating element located on or within the additional dielectric membrane; and
an additional first temperature sensing element; and
optionally wherein the heating element and the additional heating element are connected in series, and/or
wherein the additional first temperature sensing element and the first temperature sensing element are connected in series; and
optionally wherein the heating element and the additional heating element are configured to operate at different temperatures.

10. The fluid sensor according to claim 2, further comprising a covering located on a surface of the sensor, wherein the covering defines a fluid channel above the first dielectric membrane, and the covering comprises a hole configured to allow fluid to travel from an outer surface of the covering to the fluid channel above the dielectric membrane.

11. The fluid sensor according to claim 2, further comprising a further temperature sensing element located outside the dielectric membrane.

12. The fluid sensor according to claim 2, further comprising an additional first temperature sensing element outside the first dielectric membrane and an additional second temperature sensing element located on or within the first dielectric membrane.

13. The fluid sensor according to claim 2, further comprising a first additional temperature sensing element and a second additional temperature sensing element, the first and second additional temperature sensing elements located on or within the first dielectric membrane, wherein the heating element is positioned between the first additional temperature sensing element and the second additional temperature sensing element.

14. A sensor assembly comprising the fluid sensor of claim 2 and an application specific integrated circuit (ASIC) coupled to the sensor.

15. A sensor assembly comprising:
a flow sensor housing; and
a sensor according to claim 2 located within the flow sensor housing.

16. The sensor assembly comprising the fluid sensor of claim 2, wherein the fluid sensor is packaged on a printed circuit board in a flip-chip configuration.

17. A method of measuring a concentration or composition of a fluid using the fluid sensor of claim 2, the method comprising:
measuring a differential signal between the first and second temperature sensing elements; and
determining the concentration of a fluid or particular fluid components based on the differential signal.

18. The method according to claim 17, comprising applying an electrical bias to the heating element, wherein applying an electrical bias to the heating element comprises applying an electrical bias such that the differential signal between the first temperature sensing element and the second temperature sensing element is minimised.

19. The method according to claim 17, comprising:
driving the heating element in pulse mode or AC mode to modulate the temperature of the heating element to vary the differential signal; and
using the differential signal to selectively differentiate between different fluid components and/or determine the concentration of the different fluid components; and optionally
wherein differentiating between different fluid components and/or determining the concentration of the different components comprises using a neural network.

20. The method according to claim 17, wherein the method comprises:
applying a modulated function to the heating element, the first temperature sensing element, or the second temperature sensing element;
measuring the modulation, a time delay, or a phase shift of the differential signal between the first temperature sensing element and the second temperature sensing element; and
determining a concentration or composition of the fluid using the measured modulation, time delay or phase shift.

21. A fluid sensing system comprising:
the fluid sensor according to claim 2; and
a controller configured to:
measure a differential signal between the first and second temperature sensing elements; and
determine the concentration of a fluid or particular fluid components based on the differential signal.

22. The fluid sensor according to claim 2, wherein the heating element is configured to operate as the second temperature sensing element.

23. A fluid sensor for sensing a concentration or composition of a fluid, the sensor comprising:
a semiconductor substrate comprising a first etched portion and a second etched portion, wherein the first etched portion and the second etched portion are substantially identical in size and shape;
a dielectric region located on the semiconductor substrate, wherein the dielectric region comprises a first dielectric membrane located over the first etched portion of the semiconductor substrate and a second dielectric membrane located over the second etched portion of the semiconductor substrate;
a single active heating element, wherein the active heating element is located on or within the first dielectric membrane;
a first temperature sensing element located on or within the second dielectric membrane and positioned away from the first etched portion; and
a second temperature sensing element located on or within the first dielectric membrane
wherein a separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

24. The fluid sensor according to claim 23, wherein the sensor further comprises an auxiliary structure located within the second dielectric membrane, wherein the auxiliary structure is electrically isolated, and
wherein the auxiliary structure is configured such that the first dielectric membrane and the second dielectric membrane have the same mechanical and thermal stress properties.

25. A method of manufacturing a fluid sensor, the method comprising:
forming a first dielectric membrane located over a first etched portion of a semiconductor substrate semiconductor substrate comprising a first etched portion;
forming a heating element located on or within the first dielectric membrane;
forming a first temperature sensing element spatially separated from the heating element, wherein the first temperature sensing element is located outside of the first dielectric membrane and positioned away from the first etched portion;
forming a second temperature sensing element located on or within the first dielectric membrane; and
positioning the first and second temperature sensing elements such that a separation between the second temperature sensing element and the first temperature sensing element introduces a temperature difference between the second temperature sensing element and the first temperature sensing element, such that in use a differential signal between the first temperature sensing element and the second temperature sensing element is indicative of a concentration or composition of the fluid based on a thermal conductivity of a fluid.

\* \* \* \* \*